US012780881B2

(12) United States Patent
Hur et al.

(10) Patent No.: US 12,780,881 B2
(45) Date of Patent: Nov. 3, 2026

(54) ATRANORIN BIOSYNTHESIS GENE DERIVED FROM LICHENS AND USES THEREOF

(71) Applicant: INDUSTRY-ACADEMIC COOPERATION FOUNDATION OF SUNCHON NATIONAL UNIVERSITY, Suncheon-si (KR)

(72) Inventors: Jae Seoun Hur, Suncheon-si (KR); Won Yong Kim, Suncheon-si (KR); Hyung Ho Ha, Suncheon-si (KR); Hangun Kim, Gwangju (KR)

(73) Assignee: INDUSTRY-ACADEMIC COOPERATION FOUNDATION OF SUNCHON NATIONAL UNIVERSITY, Suncheon-si (KR)

( * ) Notice: Subject to any disclaimer, the term of this patent is extended or adjusted under 35 U.S.C. 154(b) by 106 days.

(21) Appl. No.: 18/567,890

(22) PCT Filed: Jun. 7, 2022

(86) PCT No.: PCT/KR2022/008015
§ 371 (c)(1),
(2) Date: Dec. 7, 2023

(87) PCT Pub. No.: WO2022/260402
PCT Pub. Date: Dec. 15, 2022

(65) Prior Publication Data

US 2025/0368695 A1 Dec. 4, 2025

(30) Foreign Application Priority Data

Jun. 7, 2021 (KR) ........................ 10-2021-0073669
May 16, 2022 (KR) ........................ 10-2022-0059678

(51) Int. Cl.
*C07K 14/41* (2006.01)
*C12N 1/145* (2026.01)
*C12N 1/21* (2006.01)
*C12N 15/80* (2006.01)
*C12P 7/62* (2022.01)
*C12R 1/645* (2006.01)

(52) U.S. Cl.
CPC .............. *C07K 14/41* (2013.01); *C12N 1/145* (2021.05); *C12N 15/80* (2013.01); *C12P 7/62* (2013.01); *C12R 2001/645* (2021.05)

(58) Field of Classification Search
None
See application file for complete search history.

(56) References Cited

U.S. PATENT DOCUMENTS

2014/0094514 A1* 4/2014 Yim .................... C07D 321/10 549/310

OTHER PUBLICATIONS

GenBank, Accession No. MZ277879, 2021, www.ncbi.nlm.nih.gov. (Year: 2021).*
Ravaglia et al., In Vitro Radical-Scavenging Activity, Toxicity Against A. salina, and NMR Profiles of Extracts of Lichens Collected From Brazil and Antarctica, Quim. Nov. 37, 2014, 1015-21. (Year: 2014).*
GenBank, Accession No. MZ277878, 2021, www.ncbi.nlm.nih.gov. (Year: 2021).*
GenBank, Accession No. MZ277877, 2021, www.ncbi.nlm.nih.gov. (Year: 2021).*
Wonyong Kim et al., "Linking a Gene Cluster to Atranorin, a Major Cortical Substance of Lichens, through Genetic Dereplication and Heterologous Expression", mBio, vol. 12, Issue 3, Jun. 22, 2021.
Mark J. Calcott et al., "Secondary metabolism in the lichen symbiosis", Chem. Soc. Rev., 2018, 47, 1730-1760, DOI: 10.1039/c7cs00431a.
Daniele Armaleo et al., "Insights from the first putative biosynthetic gene cluster for a lichen depside and depsidone", Mycologia, 103(4), 2011, pp. 741-754, Dec. 28, 2010, DOI: 10.3852/10-335.
E.Neumann et al., "Gene transfer into mouse lyoma cells by electroporation in high electric fields", The EMBO Journal, vol. 1 No.7 pp. 841-845, 1982.

* cited by examiner

*Primary Examiner* — Todd M Epstein
(74) *Attorney, Agent, or Firm* — LEX IP MEISTER, PLLC

(57) ABSTRACT

The present invention relates to an atranorin biosynthesis gene derived from a lichen *Stereocaulon alpinum*, an *Ascochyta rabiei* ATR-11 strain (Accession Number: KACC 83048BP) for producing atranorin into which the gene is introduced, and a method of producing atranorin using the above strain. A lichen-derived metabolite, particularly atranorin, may be produced from the *Ascochyta rabiei* ATR-11 strain into which the atranorin biosynthesis gene according to the present invention is introduced. Atranorin produced from the above strain can be utilized and industrialized in a variety of ways, such as pharmaceutical compositions, food compositions, health functional foods, and feed compositions.

5 Claims, 6 Drawing Sheets

Specification includes a Sequence Listing.

ATRANORIN BIOSYNTHESIS GENE DERIVED FROM LICHENS AND USES THEREOF

REFERENCE TO A SEQUENCE LISTING

The contents of the electronic sequence listing (JPK20230113US_sequence_listing_revised.txt; Size: 45,848 bytes; and Date of Creation: Mar. 6, 2025) is herein incorporated by reference in its entirety. The contents of the electronic sequence listing in no way introduces new matter into the specification.

TECHNICAL FIELD OF THE INVENTION

The present invention relates to an atranorin biosynthesis gene derived from a lichen and a use thereof. More specifically, it relates to an atranorin biosynthesis gene derived from *Stereocaulon alpinum*, an *Ascochyta rabiei* ATR-11 strain (Accession Number: KACC 83048BP) for producing atranorin into which the gene is introduced, and a method of producing atranorin using the above strain.

BACKGROUND ART OF THE INVENTION

Lichens play significant roles in ecosystem function and comprise about 20% of all known fungi. Polyketide-derived natural products accumulate in the cortical and medullary layers of lichen thalli, some of which play key roles in protection from biotic and abiotic stresses (herbivore attacks and UV irradiation). To date, however, no single lichen product has been linked to respective biosynthetic genes with genetic evidence.

Lichen-forming fungi (LFF) live in symbiosis with photosynthetic partners, green algae, or cyanobacteria, sometimes with both, and LFF are currently estimated to comprise about 20% of all known Fungi. Lichen symbiosis is one of the most successful mutualisms that enable these organisms to adapt to extremely harsh habitats. A conglutinated, often pigmented, cortical layer made up of dense fungal hyphae provides photosynthetic partners with mechanical stabilization, and algal cells enveloped by hyphae from the medulla provide nutrients to LFF by means of photosynthesis. Secondary metabolites (SMs) of polyketide origin, namely anthraquinones, depsides, depsidones, and dibenzofurans (such as usnic acid), accumulate in cortical or medullary layers of lichen thalli (Calcott M J et. al., *Chem Soc Rev.,* 47:1730-1760, 2018). The ecological roles of these lichen SMs are largely unknown, but some studies provide evidence that cortical substances have contributed to habitat expansion and defense from herbivore attacks.

Depsides and depsidone series compounds are widespread in lichens as cortical and medullary substances, many of which are exclusively found in lichens. Lichen depsides are formed by dimerization of either orsellinic acid or 3-methylorsellinic acid (3MOA), and subsequent oxidation of depsides affords tricyclic scaffolds for depsidones. These compounds further undergo different combinations of modification within orsellinic acid and 3MOA moieties, such as alkylation, chlorination, hydroxylation, and O-methylation, yielding hundreds of structurally diverse compounds. For this, depsides/depsidones biosynthetic pathways in lichens could be a model system for studying substrate specificity of biosynthetic enzymes resulting in chemodiversity. Thus far, however, ascribing specific biosynthetic genes to cortical or medullary substance has been slow in lichens, due to a paucity of genetic information on LFF and lack of molecular tools for manipulating LFF recalcitrant to genetic transformation.

Non-reducing iterative type I polyketide synthases (NR-PKSs) are multi-domain enzymes and has been grouped into seven or eight major groups by protein sequence similarity and PKS domain architecture. Orsellinic acid and 3MOA are basic scaffolds for many different SMs in bacteria, fungi and plants, and biosynthesized by NR-PKSs in a filamentous fungus, *Aspergillus nidulans*, yet only predictions have been made for two NR-PKSs to be responsible for the biosynthesis of the basic units in lichens. Atranorin (a 3MOA-derived depside) and usnic acid (a dibenzofuran) are the most common cortical substances of macrolichens, and have attracted great attention because of their taxonomic, ecological, and pharmaceutical importance. Several studies have ascribed an NR-PKS to usnic acid with high likelihood. However, the effort was unsuccessful for heterologous expression of the putative usnic acid PKS gene in *A. oryzae*, and thus its precise function remains to be determined.

In recent years, SM research has benefited extensively from genome mining approaches in bacteria, fungi, and plants Antarctic lichens Cladoniaceae is one of the largest families of LFF and closely related to Stereocaulaceae. Historically, chemotaxonomy has been used as a polyphasic approach to resolve and delimit species boundaries in Cladoniaceae, and the genus *Cladonia* has been a model for studying PKS genes for the biosynthesis of cortical and medullary substances (Armaleo D et. al., *Mycologia,* 103: 741-754, 2011).

The present inventors classified lichen polyketide synthases (PKS) and reconstructed the biosynthetic pathway of atranorin, which is the main cortical substance of lichen, in a heterologous host. Accordingly, the present inventors completed the present invention by securing a gene responsible for the biosynthesis of atranorin, a lichen cortical material, and constructing a new heterologous expression system into which the gene is introduced and developing a new strain for producing atranorin.

PRIOR ART DOCUMENTS

Non-Patent Documents (1) Calcott M J et. al., Chem Soc Rev., 47:1730-1760, 2018
(2) Armaleo D et. al., Mycologia, 103:741-754, 2011

DISCLOSURE

Technical Problem

An object of the present invention is to provide an atranorin biosynthesis gene consisting of one or more selected from the group consisting of SEQ ID NO: 1, SEQ ID NO: 3, and SEQ ID NO: 5.

Another object of the present invention is to provide a recombinant expression vector for producing metabolite derived from a lichen, including the atranorin biosynthesis gene.

Still another object of the present invention is to provide a recombinant microorganism transformed with the recombinant expression vector.

Yet another object of the present invention is to provide a method of producing a metabolite derived from lichens, includes a step of culturing the recombinant microorganism.

Yet another object of the present invention is to provide *Ascochyta rabiei* ATR-11 strain (Accession Number: KACC 83048BP).

Yet another object of the present invention is to provide a method of producing atranorin, including a step of culturing the strain.

Technical Solution

In order to achieve the above object, the present invention provides an atranorin biosynthesis gene consisting of one or more species selected from the group consisting of SEQ ID NO: 1, SEQ ID NO: 3, and SEQ ID NO: 5.

Additionally, the present invention provides a recombinant expression vector for producing metabolite derived from a lichen, including the atranorin biosynthesis gene.

Additionally, the present invention provides a recombinant microorganism transformed with the recombinant expression vector.

Additionally, the present invention provides a method of producing a metabolite derived from lichens, includes a step of culturing the recombinant microorganism.

Additionally, the present invention provides *Ascochyta rabiei* ATR-11 strain (Accession Number: KACC 83048BP).

Additionally, the present invention provides a method of producing atranorin, including a step of culturing the strain.

Advantages Effects

A heterologous expression system into which a lichen-derived atranorin biosynthesis gene according to the present invention is introduced is constructed, and lichen-derived metabolites, especially atranorin, can be biosynthesized from the *Ascochyta rabiei* ATR-11 strain by applying the same. Atranorin produced from the above strain can be utilized and industrialized in a variety of ways, such as pharmaceutical compositions, food compositions, health functional foods, and feed compositions.

DETAILED DESCRIPTION

Depsides and depsidones series compounds of polyketide origin accumulate in the cortical or medullary layers of lichen thalli. Despite the taxonomic and ecological significance of lichen chemistry and its pharmaceutical potentials, there has been no single genetic evidence linking biosynthetic genes to lichen substances. Thus, the present inventors systematically analyzed lichen polyketide synthases (PKSs) for categorization and identification of biosynthetic gene cluster (BGC) involved in depside/depsidone production. Our in-depth analysis of the inter-species PKS diversity in the genus *Cladonia* and a related Antarctic lichen *Stereocaulon alpinum* identified 45 BGC families, linking lichen PKSs to 15 previously characterized PKSs in non-lichenized fungi. Among these, the present inventors identified highly syntenic BGCs found exclusively in lichens producing atranorin (a depside). Heterologous expression of the putative atranorin PKS (coined atr1) yielded 4-O-demethylbarbatic acid found in many lichens as a precursor compound, indicating an intermolecular cross-linking activity of the Atr1 for depside formation. Subsequent introductions of tailoring enzymes into the heterologous host yielded atranorin, one of the most common cortical substances of microlichens. Phylogenetic analysis of fungal PKS revealed that the Atr1 is placed in a novel PKS clade including two conserved lichens specific PKS families likely involved in biosynthesis of depsides and depsidones. Here, the present inventors provide a comprehensive catalog of PKS families of the genus *Cladonia* and functionally characterized a biosynthetic gene cluster from lichens, establishing a cornerstone for studying genetics and chemical evolution of diverse lichen substances.

Novel Atranorin Biosynthesis Gene

As one aspect, the present invention provides an atranorin biosynthesis gene consisting of one or more selected from the group consisting of SEQ ID NO: 1, SEQ ID NO: 3, and SEQ ID NO: 5.

The term "atranorin" used in the present specification has a chemical formula name of 3-hydroxy-4-methoxycarbonyl-2,5-dimethylphenyl-3-formyl-2,4-dihydroxy-6-methyl benzoate, and has a structural formula of [Formula 1] shown below. Such atranorin may be derived from thalli as a secondary metabolite of thalli. The atranorin has been reported to have an effect of inhibiting lung cancer metastasis.

[Formula 1]

Figure 4:
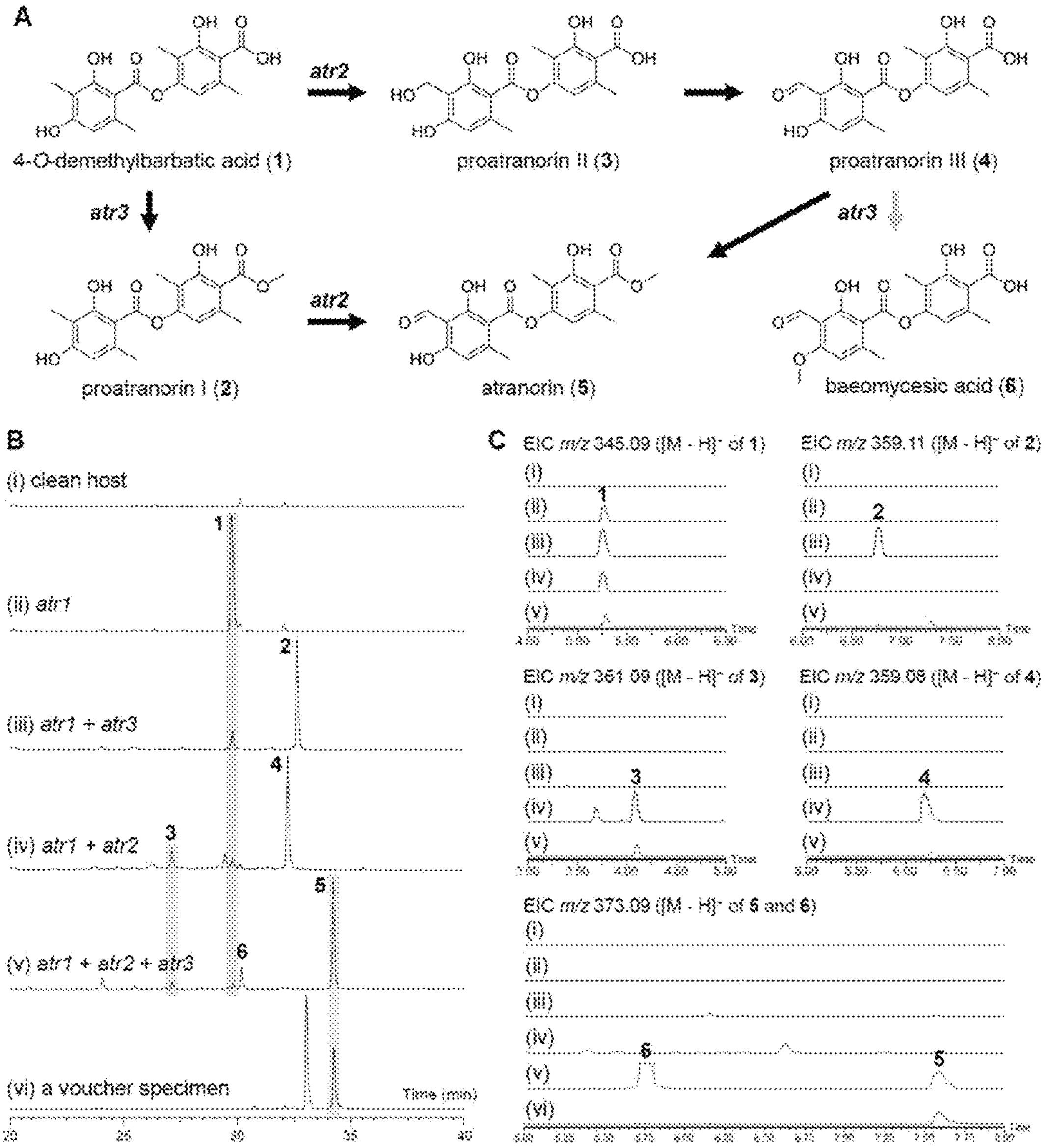
FIG. 4 shows the results of functional validation of atranorin BGC. (A) A proposed biosynthetic pathway for atranorin. (B) HPLC profiles of culture extracts of a "clean host" expressing different sets of biosynthetic genes of the atranorin BGC: with no introduced gene (i), with atr1 only (ii), with atr1 and atr3 (iii), with atr1 and atr2 (iv), and with atr1, atr2, and atr3 (v). The acetone extract of an authentic voucher specimen for the genome sequenced *Stereocaulon alpinum* contains atranorin and lobaric acid ($t_R$=33.1 min) (vi). (C) Extracted ion chromatograms (EIC) with the indicated m/z values for the compounds 1-6.

See atranorine (compound 5) in FIG. 4A.

Atranorin of the present invention may be used in a meaning of including analogues and derivatives of atranorin.

The term "thallus" used in the present specification refers to a trophosome of lichens for seredium, isidium or clonal propagation, consisting of cells of lichen symbiotic algae or cyanobacteria and hyphae of a lichen-forming fungus.

The term "lichen" used in the present specification refers to a symbiont living as a complex of fungi (mycobionts) and algae (photobionts), and it has extremely diverse shapes, sizes, and colors, inhabiting mainly on rocks, barks of tree, and soil. The lichens produce primary and secondary metabolites such as didymic acid, strepsilin, sodium usnate, lecanoric acid, and psoromic acid which have excellent bioactivity for antimicrobials (fungi, bacteria, viruses), herbicides, anti-cancer agents, immunomopotentiation, and amelioration of mental illnesses. Therefore, from old times, lichens have been traditionally used as a raw material for foods and medicines in both East and West of the world.

In the present invention, the atranorin biosynthesis gene is a secondary metabolite derived from a lichen, for example, a gene capable of inducing the expression of atranorin, and may consists of one or more selected from the group consisting of SEQ ID NO: 1, SEQ ID NO: 3, and SEQ ID NO: 5. The lichen may be *Stereocaulon alpinum* but is not limited thereto.

The base sequence represented by SEQ ID NO: 1 may be named as atr1 gene (NCBI Genbank No. MZ277879.1); the base sequence represented by SEQ ID NO: 3 as atr2 gene (NCBI Genbank No. MZ277878.1); and the base sequence represented by SEQ ID NO: 5 as atr3 gene (NCBI Genbank No. MZ277877.1).

In addition, the base sequence represented by SEQ ID NO: 1 may be encoded as an atr1 protein (NCBI Genbank No. QXF68953.1) consisting of an amino acid sequence of SEQ ID NO: 2. The base sequence represented by SEQ ID NO: 3 may be encoded as an atr2 protein (NCBI Genbank No. QXF68952.1) consisting of an amino acid sequence of SEQ ID NO: 4. The base sequence represented by SEQ ID NO: 5 may be encoded as an atr3 protein (NCBI Genbank No. QXF68951.1) consisting of an amino acid sequence of SEQ ID NO: 6.

Recombinant Expression Vector for Producing Lichen-Derived Metabolites.

As another aspect, the present invention provides a recombinant expression vector for producing a metabolite derived from a lichen, including an atranorin biosynthesis gene consisting of one or more selected from the group consisting of SEQ ID NO: 1, SEQ ID NO: 3, and SEQ ID NO: 5.

The "atranorin biosynthesis gene" is as described above.

The term "vector" used in the present specification refers to a DNA preparation containing a specific gene operably linked to a suitable regulatory sequence to enable expression of a target protein in a suitable host, wherein the regulatory sequence includes a promoter capable of initiating transcription, an arbitrary operator sequences for regulating the transcription, a sequence encoding a suitable mRNA ribosome binding site, and a sequence regulating the termination of transcription and translation. After being transformed into a suitable host cell, a vector may be replicated or may function independently of the host genome, and it may be integrated into the genome itself. The vector of the present invention may be prepared using a genetic recombination technology well known in the technical field, and enzymes generally known in the technical field are used for site-specific DNA cleavage and ligation.

The term "expression vector" used in the present specification refers to a vector into which a lichen-derived atranorin biosynthesis gene is introduced, wherein it means a recombinant expression vector capable of expressing a lichen-derived metabolite, prepared by introducing a lichen-derived atranorin biosynthesis gene to a heterologous strain, in order to artificially express lichen-derived metabolites that may not be expressed in heterologous microorganisms or host cells on their own.

Specifically, the expression vector means a vector capable of expressing a lichen-derived metabolite such as atranorin, which is a secondary metabolite derived from lichens, as well as 4-O-demethylbarbatic acid, proatranorin I, proatranorin II, proatranorin III, and baeomycesic acid, in heterologous microorganisms or host cells by the introduced atranorin biosynthesis gene. In the present invention, an expression vector may be used interchangeably with 'vector' or 'recombinant expression vector.

The expression vector may preferably include one or more selectable markers. The marker is a nucleic acid sequence that has the characteristics that it may be selected by a conventional chemical method and includes all genes that may distinguish transformed cells from non-transformed cells. Examples include antibiotic resistance genes such as ampicillin, kanamycin, G418, bleomycin, hygromycin, chloramphenicol, and apramycin, but are not limited thereto, and it may be appropriately selected by one of ordinary skill in the art.

In one embodiment of the present invention, a vector into which an atranorin biosynthesis gene derived from *Stereocaulon alpinum* is introduced may be transformed into a heterologous chickpea blight fungus *Ascochyta rabiei* to heterologously express lichen-derived metabolites.

Recombinant Microorganism Loaded with a Recombinant Expression Vector Containing an Atranorin Biosynthetic Gene In another aspect, the present invention provides a recombinant microorganism transformed with the above recombinant expression vector.

The recombinant expression vector is as described above.

The term "transformation" used in the present specification refers to a change in the genetic properties of an organism by an externally given DNA. In particular, in the present invention, it refers to introducing a vector including a specific gene, that is, a lichen-derived atranorin biosynthesis gene, to a specific heterologous microorganism so that the gene may be expressed in the specific heterologous microorganism.

The recombinant expression vector is transformed into a specific heterologous microorganism to produce a recombinant microbial strain. At this time, the transformation method may be used without any particular limitation as long as it is a known technology. For example, a calcium chloride method or an electroporation method (Neumann, et al., *EMBO J.,* 1:841, 1982) may be used for transformation.

The specific heterogeneous microorganism may be used without limitation as long as it is a microorganism or host cell that widely known in the art. Microorganisms or host cells with a high efficiency of introducing and expressing a lichen-derived atranorin biosynthesis gene of the present invention may be used, and for example, they may include fungi, bacteria, and yeast.

Specifically, the recombinant microorganism may be a fungus, and more specifically, it may be *Ascochyta rabiei.*

More specifically, the recombinant microorganism may be *Ascochyta rabiei* ATR-11 strain (Accession Number: KACC83048BP).

Method of Producing a Lichen-Derived Metabolite

In another aspect, the present invention provides a method of producing a lichen-derived metabolite, including a step of culturing the recombinant microorganism.

As described above, the recombinant microorganism may be a recombinant microorganism into which a recombinant expression vector for producing a lichen-derived metabolite, including an atranorin biosynthesis gene consisting of one or more selected from the group consisting of SEQ ID NO: 1, SEQ ID NO: 3, and SEQ ID NO: 5, is introduced.

The recombinant microorganism may be one producing one or more lichen-derived metabolites selected from the group consisting of 4-O-demethylbarbatic acid, proatranorin I, proatranorin II, proatranorin III, atranorin, and baeomycesic acid, but is not limited thereto.

Culture conditions of the recombinant microorganism for producing a lichen-derived metabolite may vary depending on the type of transformed recombinant microorganism or host cell. Depending on the type of the recombinant microorganism or host cell, culture may be performed according to conditions known to one of ordinary skill in the art, that is under conventional temperature conditions of, for example, 25 to 40° C., and under conventional pH conditions, for example, pH 6 to 8. Under these conditions, the above lichen-derived metabolites may be mass-produced from a recombinant microorganism or host cell with a high yield.

As described above, as the recombinant microorganism or hos cell, microorganisms or host cells known in the art with a high efficiency of introducing and expressing a lichen-derived atranorin biosynthesis gene may be used without a limitation. Specifically, the recombinant microorganism may be a fungus, and more specifically, it may be *Ascochyta rabiei.* More specifically, the recombinant microorganism may be *Ascochyta rabiei* ATR-11 strain (Accession Number: KACC 83048BP).

Additionally, as a medium used for culturing (or fermenting) the recombinant microorganism or host cell, one that appropriately satisfies the requirements of a specific microbial strain or host cell may be appropriately selected. The medium may include various carbon sources, nitrogen sources, phosphorus sources, and trace element components. Examples of carbon sources in the medium may be sugars and carbohydrates such as glucose, saccharose, lactose, fructose, maltose, starch, and cellulose, oils, and fats such as soybean oil, sunflower oil, castor oil, and coconut oil, fatty acids such as palmitic acid, stearic acid, and linoleic acid, alcohols such as glycerol and ethanol, and organic acids such as acetic acid, but are not limited thereto. These substances may be used individually or in mixtures. The carbon source may be glycerol, glucose, or a combination thereof. Examples of nitrogen sources in the medium may be peptone, yeast extract, broth, malt extract, corn steep liquor, soybean meal, and urea or inorganic compounds, for example, ammonium sulfate, ammonium chloride, ammonium phosphate, ammonium carbonate, and ammonium nitrate, but are not limited thereto. Nitrogen sources may also be used individually or in mixtures. Examples of phosphorus sources may be potassium dihydrogen phosphate or dipotassium hydrogen phosphate or corresponding sodium-containing salts but are not limited thereto. In addition, a culture medium may include metal salts necessary for growth, such as magnesium sulfate or iron sulfate, or may include essential growth substances such as amino acids and vitamins but is not limited thereto. The above raw materials may be added to a culture batchwise or continuously in an appropriate manner during a culture process.

Additionally, according to the necessary, the pH of the culture may be adjusted by using basic compounds such as sodium hydroxide, potassium hydroxide, and ammonia, or acid compounds such as phosphoric acid or sulfuric acid in an appropriate manner. In addition, foam generation may be suppressed by using an antifoaming agent such as fatty acid polyglycol ester. The temperature of the culture may usually be maintained at 20° C. to 45° C., or 25° C. to 40° C. The culture may be performed continuously until the maximum production of a desired metabolite, for example, one or more lichen-derived secondary metabolites selected from the group consisting of 4-O-dimethylbarbatic acid, proatranorin I, proatranorin II, proatranorin III, atranorin, and baeomycesic acid, is obtained.

The method of producing a lichen-derived metabolite provided in the present specification may further include a step of recovering or isolating a produced lichen-derived secondary metabolite after the step of culturing described above. A method of recovering or isolating a lichen-derived secondary metabolite produced from a recombinant strain or a culture thereof may be selected from methods that are widely known in the art. Examples of methods of recovering 4-O-dimethylbarbatic acid, proatranorin I, proatranorin II, proatranorin III, atranorin or baeomycesic acid include centrifugation, sonication, filtration, ion exchange chromatography, high-performance liquid chromatography (HPLC), gas chromatography (GC), and the like, but are not limited to these examples.

The lichen-derived metabolites provided in the present specification may be produced from a recombinant microorganism transformed by selectively introducing one or more of the above-mentioned atranorin biosynthesis genes (see Scheme 1 below).

[Scheme 1]

See FIG. 4A.

In one embodiment of the present invention, 4-O-dimethylbarbatic acid may be produced by culturing under predetermined conditions a recombinant microorganism into which the atr1 gene consisting of the base sequence of SEQ ID NO: 1 is introduced. At this time, the recombinant microorganism is not limited thereto, but may be phytopathogenic fungus *Ascochyta rabiei* (*As. rabiei*).

In one embodiment of the present invention, proatranorin I may be produced by culturing under predetermined conditions a recombinant microorganism into which the atr1 gene consisting of the base sequence of SEQ ID NO: 1 and the atr3 gene consisting of the base sequence of SEQ ID NO: 5 are introduced. At this time, the recombinant microorganism is not limited thereto, but may be phytopathogenic fungus *Ascochyta rabiei* (*As. rabiei*).

In one embodiment of the present invention, proatranorin II and proatranorin III may be produced by culturing under predetermined conditions a recombinant microorganism into which the atr1 gene consisting of the base sequence of SEQ ID NO: 1 and the atr2 gene consisting of the base sequence of SEQ ID NO: 3 are introduced. At this time, the recombinant microorganism is not limited thereto, but may be phytopathogenic fungus *Ascochita rabiei* (*As. rabiei*).

In one embodiment of the present invention, atranorin may be produced by culturing under predetermined conditions a recombinant microorganism into which the atr1 gene consisting of the base sequence of SEQ ID NO: 1, the atr2 gene consisting of the base sequence of SEQ ID NO: 3, and the atr3 gene consisting of the base sequence of SEQ ID NO: 5 are introduced. At this time, the recombinant microorganism is not limited thereto, but may be phytopathogenic fungus *Ascochita rabiei* (*As. rabiei*).

*Ascochyta rabiei* ATR-11 Strain for Producing Atranorin

As another aspect, the present invention provides *Ascochyta rabiei* ATR-11 strain (Accession Number: KACC83048BP).

The term "*Ascochyta rabiei*" used in the present specification refers a phytopathogenic fungus that causes chickpea blight, and it is a heterologous host microorganism used to introduce the lichen-derived atranorin biosynthesis gene described above.

The *Ascochyta rabiei* ATR-11 strain (Accession Number: KACC83048BP) is a strain for producing atranorin, deposited to the Korean Agricultural Culture Collection (KACC) of the National Institute of Agricultural Sciences on May 28, 2021, with the Accession Number KACC 83048BP.

Specifically, the *Ascochyta rabiei* ATR-11 strain is the above-described strain into which an atranorin biosynthesis gene consisting of one or more selected from the group consisting of SEQ ID NO: 1, SEQ ID NO: 3, and SEQ ID NO: 5 is introduced, and it is capable of producing atranorin. Atranorin produced from the above strain can be utilized and industrialized in a variety of ways, such as pharmaceutical compositions, food compositions, health functional foods, and feed compositions.

Method of Producing Atranorin Using *Ascochyta rabiei* ATR-11 Strain

As another aspect, the present invention provides a method for producing atranorin, including a step of culturing *Ascochyta rabiei* ATR-11 strain (Accession Number: KACC83048BP).

The *Ascochyta rabiei* ATR-11 strain (Accession Number: KACC 83048BP) is as described above.

The culture conditions of the *Ascochyta rabiei* ATR-11 strain (Accession Number: KACC 83048BP) may be a temperature of 15 to 25° C. and a culture duration of 7 to 21 days, preferably, a temperature of 18 to 22° C. and a culture duration of 14 to 18 days, but are not particularly limited thereto.

In addition, culturing of the *Ascochyta rabiei* ATR-11 strain (Accession Number: KACC 83048BP) may be performed by using a natural medium or synthetic medium including carbon sources, nitrogen sources, inorganic salts, and the like that may be efficiently utilized by the strain. Carbon sources that may be used include carbohydrates such as glucose, fructose, sucrose, soybean powder, peanut powder, wheat flour, corn powder, dextrin, corn meal, and fructose syrup; starch and hydrolysate of starch; organic acids such as acetic acid and propionic acid; alcohols such as ethanol, propanol, and glycerol; and oils such as soybean oil, olive oil, canola oil, peanut oil, and fish oil. Nitrogen sources include ammonia; ammonium salts of inorganic or organic acids such as ammonium chloride, ammonium sulfate, ammonium acetate, and ammonium phosphate; peptone, meat extract, yeast extract, corn steeping liquid, casein hydrolysate, soybean extract, soybean hydrolysate; and various fermented cells and decomposition products thereof. Amino acids include monosodium glutamate, methionine, lysine, leucine, cysteine, and valine. Inorganic salts include potassium dihydrogen phosphate, dipotassium hydrogen phosphate, magnesium phosphate, magnesium sulfate, sodium chloride, manganese sulfate, copper sulfate, calcium carbonate, and the like.

The pH of the medium is preferably maintained in a range of 3.0 to 9.0 during culture. The pH of the medium may be adjusted with inorganic or organic acids, alkaline solutions, urea, calcium carbonate, ammonia, and the like.

After culturing the *Ascochyta rabiei* ATR-11 strain (Accession Number: KACC 83048BP), various known methods may be used to isolate, purify, and recover atranorin therefrom. For example, after removing the bacterial cells by centrifugation, isolation and purification may be performed by appropriate known methods such as salting out, ethanol precipitation, ultrafiltration membrane, gel filtration chromatography, ion exchange column chromatography, or a combination thereof.

Production of atranorin using the *Ascochyta rabiei* ATR-11 strain (Accession Number: KACC 83048BP) is suitable for not only lab-scale production but also large-scale production, and thus is to be commercially applied.

The atranorin may be atranorin derived from a lichen *Stereocaulon alpinum* but is not limited thereto.

EXAMPLES

Hereinafter, the constitution and effects of the present invention will be described in more detail through examples. These examples are only for illustrating the present invention, and the scope of the present invention is not limited by these examples.

Example 1: Phylogenomic Analysis

To infer the phylogeny of the genome-sequenced 29 LFF (Lichen-forming fungi) and an endophytic fungus *Cyanodermella asteris*, the present inventors pursued a coalescent-based phylogenomic approach. The culture, genome sequencing and annotation procedures for LFF were described in Example 8. Single-copy ortholog clusters (SCOs) of protein sequences deduced from the 30 annotated genomes were identified using OrthoMCL (v2.0.9) with an inflation factor of 2.5. For each of the 393 SCOs, protein sequences were aligned using MAFFT (v7.310) with the 'auto' setting, and the resulting 393 multiple sequence alignments were trimmed for poorly aligned regions using Gblocks (v0.91b) with the parameter: '-b4=5'. The RAxML program (v8.2) was used to calculate 100 maximum likelihood trees for each multiple sequence alignment. To generate coalescent-based trees, the present inventors used ASTRAL-III (v5.7.4) with two multi-locus bootstrapping options (site only resampling and gene/site resampling) and with no bootstrapping option. All trees showed the identical topology.

Example 2: Biosynthetic Gene Cluster Family Analysis

For BGC identification in the 30 genomes, the genome assembly and annotation files were processed by the antiSMASH program (v5.0+), with a parameter setting: '--minimal'. For genetic dereplication of BGCs found in the six *Cladonia* spp. and *S. alpinum*, the present inventors used the BiG-SCAPE program, in reference to the MIBiG database (v1.4). To analyze BGCs containing at least one iterative type I PKS, the present inventors modified a configuration file 'domain_whitelist.txt' to include only Pfam domains related to iterative type I PKS (PF00109 and PF02801) and ran the BiG-SCAPE program with optional arguments: '--mix' and '--hybrids-off'. Based on the Jaccard index of domain types, domain sequence similarity, and domain adjacency index, the BiG-SCAPE program calculates a similarity matrix between pairwise combinations of clusters where smaller values indicate greater BGC similarity. The present inventors evaluated BGC networks using an edge-length cutoff from 0.3-0.8 with a step of 0.1 and considered the network using a cutoff value of 0.5 as a representation of GCFs in the six *Cladonia* spp. and *S. alpinum*. Individual networks for PKS families were visualized, using a Python package NetworkX (v2.5), in that edge-width was weighted by squared similarity between a pair of BGCs calculated by BiG-SCAPE. The present inventors used the CORASON program that generates a multi-locus, approximately maximum-likelihood, phylogenetic tree of BGCs including PKS families responsible for production of lichen substances. For the PKS23 family, an OMT (Crg06815) in *C. rangiferina* was used as the query gene to search for homologous BGCs from a total of 1,527 BGCs detected in the 30 sequenced species. For the PKS1 family, a GAL4-type transcription factor (gene ID: Crg07068) in *C. rangiferina* was used as the query gene.

Example 3: Phylogenetic Analysis of Fungal NR-PKS

KS domain of iterative type I PKS has been considered evolutionarily conserved, and thus it can serve as a proxy for the similarity of the entire PKS. The present inventors identified a total of 242 PKSs from the genomes of the six *Cladonia* spp. and *S. alpinum*, among which four PKSs (Cgr01615, Cgr03964, Cgr08611, and Cmt10189; see Data Set S2) were missing a KS domain. KS domain sequences were extracted from 238 PKSs using the online tool NaPDoS and aligned using MUSCLE (v3.8.31). For clustering analysis, an all-versus-all similarity matrix for KS domains of 238 PKSs was computed using the AlignBuddy function in the BuddySuite program, with an optional argument: '-pi'. A heatmap showing percent similarity of KS domains clustered by k-means was generated using an R package Superheat. For fungal NR-PKS phylogeny, the present inventors used concatenated protein sequences of KS and PT domains of 103 NR-PKSs found in the six *Cladonia* spp. and *S. alpinum*, and 82 NR-PKSs that have been linked to known compounds in non-lichenized fungi. The present inventors initially identified 106 NR-PKSs in the six *Cladonia* spp. and *S. alpinum*, including seven NR-PKSs whose full sequences cannot be reliably defined from the current genome assembly (likely pseudogenes). Among these partial PKSs, three NR-PKSs (Cbo04702, Cma06590, and Cmt06606) lacked either KS or PT domain, and were excluded from the phylogenetic analysis. PT domains of lichen NR-PKSs were identified by aligning with those of previously characterized PKSs. A 6-methylsalicylic acid synthase (6MSAS) responsible for the biosynthesis of patulin (UniProtKB: A0A075TRC0) in *Penicillium expansum* was set to be an outgroup to fungal NR-PKS phylogeny. Also, four 6MSASs found in four *Cladonia* spp. were included in the analysis (Cbo07291, Cgr05254, Cmt10005, and Cuc03485). Protein sequences of KS and PT domains were aligned using MAFFT (v7.310) with the 'auto' setting, and spurious sequences or poorly aligned regions from each domain were trimmed using the trimAl program (v1.2), with the 'gappyout' parameter. The resulting multiple sequence alignments for KS and PT domains were concatenated with FASconCAT-G (v1.04). From the concatenated sequences, maximum-likelihood trees were computed with RA×ML (v8.2), using a gamma distribution for substitution rate across sites with a parameter setting: '-m PROTGAMMAWAG'. Nodal support was evaluated by 1,000 bootstrap replications. The final tree was rooted to the 6MSAS outgroup and annotated by iTOL (v5.7).

Example 4: Generation of a "Clean Host" from *Ascochyta rabiei*

A split-marker strategy was employed to generate a solanapyrone-minus mutant ("clean host"). A downstream region of the sol1 (1,208 bp) and an upstream region of the sol3 (1,459 bp) were amplified from gDNA of *As. rabiei* isolate AR628 (39), using L5/L3 and R5/R3 primer pairs, respectively. A hygromycin phosphotransferase gene (hph) cassette was amplified from pCB1004 plasmid, using a primer pair HYG5/HYG3. L3 and R5 primers have 27 nt-long overhang sequences complementary to the 3' and 5' end of the hph cassette, respectively, such that the amplified sol1 downstream and sol3 upstream regions can be fused to the hph cassette by overlap extension PCR. Finally, split marker constructs were amplified from the fused construct, using N5/HY-R and YG-F/N3 primer pairs. The split marker constructs were introduced into protoplasts of *As. rabiei* by polyethylene glycol-mediated genetic transformation as described in Hallen-Adams et al. Primers used in the gene replacement were listed in Table 1.

Information on the primers used in the present invention is summarized in Table 1 below.

TABLE 1

| Pirmer | Sequence (5′-3′) | No | Description |
|---|---|---|---|
| Sol1PpDS33_fwd | AGATCTCGGCACGTTTTGATCGCAAAG | 7 | sol1 promoter cloning into pDS33 |
| Sol1PpDS33_rev | AAGCTTAGTAATATCTGGCGATGAAGCGTCAG | 8 | sol1 promoter cloning into pDS33 |
| Inf_Sta046440_fwd | CAGATATTACTAAGCTCATGGCGTCTAACCATGAGGAG | 9 | PKS23 cloning into pDS35 |
| Inf_Sta046440_rev | GTAACGTTAAGTGGATCCTTACAACTAAAGCTCTCAATCAACCC | 10 | PKS23 cloning into pDS35 |
| Sta046440_check1F | GGACGATGAGAACGTCCTAG | 11 | PKS23 sequencing |
| Sta046440_check2F | CGAGTCAGGTGATCCAGTG | 12 | PKS23 sequencing |
| Sta046440_check3F | CCAATCATACTGAGCGCTG | 13 | PKS23 sequencing |
| Sta046440_check4F | CACATGTCTGTGGCTTGAG | 14 | PKS23 sequencing |
| Sta046440_check5F | CAACTCCGGTGATGATTG | 15 | PKS23 sequencing |
| Sta046440_check6F | CAACCCTTCCACATATTGAG | 16 | PKS23 sequencing |
| pII99_sol5_fwd | GAATTCAGAGCGACAGTGAAAGC | 17 | sol5 promoter cloning into pII99 |
| pII99_sol5_rev | AGATCTAGCTAGCTTGGCGTGATGTCAGTCAATGCTG | 18 | sol5 promoter cloning into pII99 (NheI enzyme site in bold) |
| pII99_tef1a_fwd | GAATTCCAGCCGAGACAGCAGAATCAC | 19 | tef1α promoter cloning into pII99 |
| pII99_tef1a_rev | AGATCTAGCTAGCGTGTTATGTTTTGTGGAATATAAAAGGG | 20 | tef1α promoter cloning into pII99 |
| Inf95_Sta04642_fwd | ATCACGCCAAGCTAGCACGATGACTTCCGTTGATACAATG | 21 | atr3 cloning into pII95 |
| Inf98_Sta04642_fwd | AAACATAACACGCTAGCACGATGACTTCCGTTGATACAATG | 22 | atr3 cloning into pII98 |
| Inf99_Sta04642_rev | GGAGACCGGCAGATCCCGTCACATGTCCGTCATAATAAC | 23 | atr3 cloning into pI195 and pII98 |
| Inf98_Sta04643_fwd | AAACATAACACGCTAGAACCATGGCTCTCCTAGACACAATTG | 24 | atr2 cloning into pII95 |
| Inf95_Sta04643_fwd | ATCACGCCAAGCTAGAACCATGGCTCTCCTAGACACAATTG | 25 | atr2 cloning into pII98 |
| Inf99_Sta04643_rev | GGAGACCGGCAGATCGAGGAGCAAAGGAACAAGGAACAG | 26 | atr2 cloning into pI195 and pII98 |

TABLE 1-continued

| Pirmer | Sequence (5′-3′) | No | Description |
|---|---|---|---|
| pII99_MK5 | CGTCAAGAGACCTACGAGACTG | 27 | Replacing nptII with ble in the plasmid tef1α::atr2/pII98 |
| pII99_MK3 | GCTATACTTCTAGGTCTTGGAAGAG | 28 | Replacing nptII with ble in the plasmid tef1α::atr2/pII98 |
| Inf_BLE_pII99_fwd | GTAGGTCTCTTGACGCATTAAGACCTCAGCGCTAGTGG | 29 | Replacing nptII with ble in the plasmid tef1α::atr2/pII98 |
| Inf_BLE_pII99_rev | GACCTAGAAGTATAGCGGTGTTACGGAGCATTCACTAGG | 30 | Replacing nptII with ble in the plasmid tef1α::atr2/pII98 |
| L5 | GAGGTCTTCACACCACAAGTTCG | 31 | Generating "clean host" |
| L3 | GGCAAAGGAATAGAGTAGATGCCGACCGGGCTCTTGCGTAGTGGTACAGATG | 32 | Generating "clean host" |
| R5 | GTTGACCTCCACTAGCTCCAGCCAAGCGAATAGGTAACAAAGCCAGCCGAG | 33 | Generating "clean host" |
| R3 | GAGAATTGCGGCGCAGGATGTTC | 34 | Generating "clean host" |
| N5 | CTGACTTTCTTCTTGCAGCCCTGC | 35 | Generating "clean host" |
| N3 | CTAACGATGTCGTTAGTCGCCTTG | 36 | Generating "clean host" |
| HYG-F | GCTTGGCTGGAGCTAGTGGAG | 37 | Generating "clean host" |
| HYG-R | CGGTCGGCATCTACTCTATTCCTT | 38 | Generating "clean host" |
| YG-F | CGATGTAGGAGGGCGTGGATATGTC | 39 | Generating "clean host" |
| HY-R | TGTAGTGTATTGACCGATTCCTTGCG | 40 | Generating "clean host" |
| P1_fwd | GGACGATGAGAACGTCCTAG | 41 | RT-PCR analysis |
| P1_rev | GAGAGTTCCTCATGCTCGTC | 42 | RT-PCR analysis |
| P2_fwd | CATCGACGACACGGAGATACTG | 43 | RT-PCR analysis |
| P2_rev | GACCGTGAGATTCTTTGAAGAGG | 44 | RT-PCR analysis |
| Actin1_fwd | CAATGGTTCGGGTATGTGCAAG | 45 | RT-PCR analysis |
| Actin1_rev | GAAGAGCGAAACCCTCGTAGAT | 46 | RT-PCR analysis |

Example 5: Heterologous Expression of the Atr1 and RT-PCR Analysis

For efficient expression of foreign genes in the "clean host", the present inventors constructed expression vectors that carry either the sol1 gene promoter (pDS35), the sol5 gene promoter (pII95), or translation elongation factor 1 alpha gene promoter (pII98). Then, the atr1, atr2 and atr3 genes were individually cloned to the expression vectors. Details on expression vector construction and cloning procedures are described in Examples 9 and 10. For heterologous expression of the atr1, the sol1::atr1/pDS35 plasmid (5-10 microgram) was used to transform the "clean host". Putative transformants were subcultured on potato dextrose agar (PDA; BD Biosciences) containing 100 μg/ml of nourseothricin sulfate (clonNAT; GoldBio). Two transformants, designated as Sta04644-T16 and Sta04644-T25, exhibited resistant to the selective agent, and were subcultured on PDA overlaid with a nylon membrane for RNA extraction. After two weeks of culture, mycelia growing on PDA were scraped off from the nylon membrane with a single-edge razor blade and were subjected to total RNA extraction. Total RNA was extracted from hyphae ground in liquid nitrogen, using TRIzol reagent (Thermo Fisher Scientific), according to the manufacturer's instruction, with additional extraction steps: one phenol (pH 4.6)-chloroform-isoamyl alcohol (25:24:1) extraction followed by one chloroform extraction step after the initial TRIzol-chloroform phase separation. RNA pellets were dissolved in 88 μL of nuclease-free water and subjected to genomic DNA digestion by DNase treatment (Qiagen). Then, RNA samples were concentrated using the RNA Clean & Concentrator (Zymo research). The present inventors confirmed expression and intron splicing of the atr1 with four introns in RT-PCR analysis. Two primer sets were designed: (i) to amplify a flanking region of the first intron located at the 5' region of the atr1 coding sequence, and (ii) to amplify a region harboring the second, third and fourth (the last) introns at the 3' region of the atr1 coding sequence. Two hundred nanogram of total RNA was reverse-transcribed, and the atr1 and actin1 (as a positive control) were amplified, using a OneStep RT-PCR kit (Qiagen). Primers used in RT-PCR analysis and plasmid constructions were listed in the above Table 1.

Example 6: Generation of a Heterologous Host Producing Atranorin

For introduction of tailoring enzymes into a atr1-expressing strain (Sta04644-T25), the four resulting plasmids (sol5::atr2/pII95, tef1α::atr2/pII98, sol5::atr3/pII95, and tef1α::atr3/pII98) were individually transformed into the Sta04644-T25 strain, and putative transformants were subcultured on PDA containing 200 μg/ml of G418 disulfate (Sigma-Aldrich). Transformants resistant to G418 disulfate were selected for metabolite identification. A strain harboring both sol1::atr1/pDS35 and sol5::atr3/pII95 was used for the generation of an atranorin-producing strain, which exhibited the greatest production of compound 2 (proatranorin), the immediate precursor of atranorin. Since a neomycin phosphotransferase II gene (nptII) cassette that confer resistance to G418 disulfate was already integrated into the strain producing compound 2, the present inventors replaced the nptII cassette in the tef1α::atr2/pII98 plasmid with a bleomycin resistant protein gene (ble), the tef1α::atr2/pII98 plasmid was amplified using a primer pair 'Inf_BLE_pII99_fwd' and 'Inf_BLE_pII99_rev', and the ble was amplified from pAC1750. Then, the two PCR products were fused, using the In-Fusion HD Cloning Kit (Takara). The resulting plasmid was transformed into the strain producing compound 2, and putative transformants were subcultured on PDA containing 200 μg/ml of Zeocin (a member of bleomycin family distributed by Thermo Fisher Scientific).

To select transformants that produce atranorin, the chemical profile of transformants resistant to Zeocin were compared to that of a *S. alpinum* voucher specimen (the Korea National Arboretum accession: KHL0017342) from which the genome-sequenced LFF had been originally isolated. Detailed methodologies for HPLC, LC-MS/MS, and NMR spectroscopic analyses for culture extracts and purified compounds were fully described in Examples 11 to 13.

Example 7: Data Availability

This whole genome shotgun project has been deposited at DDBJ/ENA/GenBank under accessions, JAFEKC000000000, JAEUBB000000000, and JAEUBA000000000 (BioProject: PRJNA693578, PRJNA693575, and PRJNA693574) for *C. borealis*, *Parmelia* cf. *squarrosa*, and *S. alpinum*, respectively. Raw LC-MS/MS data were deposited at the MassIVE database (http://massive.ucsd.edu) under the accession no. MSV000087081).

Example 8: Genome Sequencing and Annotation

LFF were isolated from *C. borealis* and *S. alpinum* collected from the King George Island, *Antarctica* (S62 deg. 13'51" W58 deg. 46'32") and *Parmelia* cf. *squarrosa* collected from Mt. Deogyu, South Korea (N35 deg. 51'24" E127 deg. 44'54"). The LFF were cultured for 3-6 months on malt extract agar media (BD Biosciences). Genomic DNAs were extracted using a standard phenol/chloroform extraction method and were sequenced on an Illumina HiSeq2000 or NovaSeq6000 instrument, generating 150 nucleotide paired-end reads. Illumina adaptors were trimmed, read quality was assessed, and contigs were assembled at Macrogen Inc. (Seoul, South Korea). The genome assemblies retrieved from the NCBI database were annotated using GenSAS (v.6.0) annotation pipeline. In brief, low complexity regions and repeats were masked using RepeatModeler (v1.0.11) and RepeatMasker (v4.0.7) (www.repeatmasker.org), setting the DNA source to 'Fungi'. A masked consensus sequence was generated on which ab initio gene prediction was performed using the following tools: (i) Augustus (v3.3.1), selecting *A. nidulans* as a trained organism, (ii) GeneMarkES (v4.33), (iii) Genscan (v1.0), using a parameter setting for Human and other vertebrates, and (iv) GlimmerM (v2.5.1), selecting *Aspergillus* as a trained organism. For homology-based prediction, the NCBI reference transcript and protein databases for Fungi were searched, using (v) BLAST+ (v2.7.1) and (vi) DIAMOND (v0.9.22), respectively. For the consensus gene model prediction using EVidenceModeler (v06-25-2012), the above-mentioned standalone gene predictions were weighted as follows: (i)—five, (ii)—ten, (iii)—one, (iv)—one, (v)—five, and (vi)—five. The genome annotations were assessed with BUSCO (v5b) using the Ascomycota_odb9 data set.

Example 9: Expression Vector Construction for PKS Expression

The pDS23 plasmid carries a nourseothricin acetyltransferase gene (nat) cassette as a selection marker and an enhanced green fluorescent protein (eGFP) under the control of the constitutive promoter of glyceraldehyde-3-phosphate dehydrogenase gene (G3PD) derived from *Aspergillus nidulans*. To replace the G3PD promoter with multiple cloning sites in pDS23, the plasmid was linearized by AvrII and HindIII restriction enzymes, and a synthetic DNA (57-bp long) harboring several restriction enzyme sites (NheI, AatII, SacI, PmeI, BglII, and SacII) was cloned between the AvrII and HindIII sites of the plasmid. The resulting plasmid was named pDS33. To generate an expression vector that carries a native promoter of *As. rabiei*, the 1,270-bp DNA fragment containing the sol1 (encoding solanapyrone synthase) gene promoter amplified from gDNA of *As. rabiei* isolate AR628 was cloned to pDS33 precut with BglII and HindIII, yielding the pDS35 plasmid. The coding sequence of atr1 (Sta04644) was amplified with a primer pair 'Inf_Sta046440_fwd' and 'Inf_Sta046440_rev' (7,829 bp) and cloned to the pDS35 linearized by HindIII and BamHI, in replace of eGFP, using the In-Fusion HD Cloning Kit (Takara), which resulted in the plasmid sol1::atr1/pDS35.

Example 10: Expression Vector Construction for Tailoring Enzyme Expression

The pII99 plasmid carries a neomycin phosphotransferase II gene (nptII) cassette as a selection marker. To generate an expression vector that carries the promoter of the sol5 (encoding a Diels-Alderase that catalyzes the last step of solanapyrone biosynthesis), the 579-bp DNA fragment containing the sol5 promoter amplified from gDNA of *As. rabiei* AR628 strain was cloned to pII99 precut with EcoRI and BglII, yielding the pII95 plasmid. To introduce an additional restriction enzyme site, the revere primer for the sol5 promoter amplification was designed to have NheI site (see Table 1). The pII95 plasmid was digested with NheI and BglII, and the PCR products of the atr3 (Sta04642) or atr2 (Sta04643) amplified from gDNA of *S. alpinum* was fused to the precut plasmid, resulting in the plasmids, sol5::atr3/pII95 and sol5::atr2/pII95. Similarly, to generate an expression vector that carries the constitutive promoter of translation elongation factor 1 alpha gene (tef1α) derived from *A. nidulans*, the plasmid pII98 was generated by cloning the 880-bp DNA fragment containing the tef1α promoter amplified from the pAC1750 plasmid into pII99, and the coding sequences plus terminator regions of the atr3 and atr2 were individually fused into the pII98 precut with NheI and BglII, generating the plasmids, tef1α::atr3/pII98 and tef1α::atr2/pII98.

Example 11: HPLC Analysis and Metabolite Purification

For metabolite extraction and profiling, transformants were grown on PDA for 2-3 weeks and the whole agar containing fungal colony was excised from the Petri dish and soaked into 10 ml of ethyl acetate in a 50 ml falcon tube. After sonication for 30 min, an aliquot of 1 ml of solution was transferred to a 1.5 ml microcentrifuge tube, evaporated to dryness, reconstituted with 100 μl of methanol, and subjected to a high-performance liquid chromatography (HPLC) analysis. Pieces of the *S. alpinum* voucher specimen (20-30 mg) were soaked into 300 μl of acetone in a 2 ml microcentrifuge tube. After sonication for 30 min, the sample was filtered through 0.4 mm syringe membrane before injection to HPLC. Chemical profiling of transformants was performed using a Prominence Modular LC-20A HPLC instrument (Shimadzu). The samples were analyzed using a YMC-Pack ODS-A (column size, 150×4.6 mm; particle size, 5 μm; pore size, 12 nm; at 40° C.) and using a photodiode array detector at 254 nm (SPD-M20A, range 180-700 nm). The mobile phase was composed of distilled water/trifluoroacetic acid (99.9:0.1, v/v) for pump A and methanol/trifluoroacetic acid (99.9:0.1, v/v) for pump B. The HPLC analysis was performed using a gradient program at a flow rate of 1.0 ml/min: 0-30 min, 20-100%; 30-40 min, 100%; 40-52 min, 20% of pump B. The present inventors used the lichen substance database for HPLC analysis to identify metabolites found in lichen specimens (15). For structural identification, the present inventors purified compounds 1, 2, and 4 from culture extracts of transformants producing the compounds as major metabolites. Twenty PDA cultures were extracted three times with ethyl acetate. Culture extracts were evaporated to dryness on a Rotavapor (Buchi), reconstituted with methanol, and subjected to preparative HPLC. Separation was achieved on a HPLC at a flow rate of 2.2 ml/min, using the Kromasil C18-column (250×10 mm, 5 μm, 10 nm; at 40° C.), with UV monitoring at 254 nm. The compound 1 was purified using 66% acetonitrile (tR=9.86 min; 9.5 mg); compound 2 was purified using 85% acetonitrile ($t_R$=9.77 min; 6.2 mg); compound 4 was purified using 80% acetonitrile (tR=9.60 min; 2.1 mg). Solvents were buffered with 0.1% trifluoroacetic acid. The purified compounds were subjected to NMR spectroscopic analyses.

Example 12: LC-MS/MS Analysis for Identifying Products

Culture extracts were 20-folds diluted with methanol and filtered with a 0.22 μm PTFE filter. The LC-MS analysis was performed on a Waters Acquity I-Class UPLC system coupled to a Waters VION IMS QTOF mass spectrometer (Waters Co.), which was equipped with an electrospray ionization interface. The mobile phase was comprised of 0.1% formic acid in water (pump A) and acetonitrile (pump B). A stepwise gradient method at a constant flow rate of 0.3 ml/min was used to elute the column with the following conditions: 20-100% of pump B (0-9 min), followed by 3 min of washing and 3 min of reconditioning. The injection volume was 2 μl. The column temperature and sample organizer were maintained at 40° C. and 20° C., respectively. Tandem MS analyses were performed in data-independent acquisition ($MS^E$), negative ion mode with the m/z 50-1500 Da range and acquisition times of 0.2 s. The low collision energy for the detection of the precursor ions was set to 6 eV, while the high collision energy for fragmentation was set to 20-40 eV. The ionization conditions were set as follows: the capillary voltage was 2.5 kV, the cone voltage was 40 V, the source temperature was 100° C., the desolvation temperature was 250° C., the cone gas flow was 0 l/h, and the desolvation gas flow was 800 l/h. High-purity nitrogen was used as the nebulizer and auxiliary gas, and argon was used as the collision gas. The $[M-H]^-$ ion of leucine enkephalin at m/z 554.2615 was used as the lock mass to ensure mass accuracy and reproducibility. MS/MS spectral data matching of major compounds detected in transformants was performed by the feature-based molecular networking workflow in GNPS after the preprocessing using MS-DIAL.

Example 13: NMR Spectroscopic Data Summary 13-1: 4-O-Demethylbarbatic Acid (Compound 1)

$^1$H NMR (400 MHz, $CD_3COCD_3$): $\delta_H$ 11.65 (s, OH), 6.73 (s, 1H), 6.47 (s, 1H), 2.68 (s, 3H), 2.63 (s, 3H), 2.12 (각각 s, 3H×2); $^{13}$C NMR (100 MHz, $CD_3COCD_3$): $\delta_C$ 170.4, 164.0, 163.3, 160.6, 153.0, 140.9, 140.7, 116.7, 116.6, 111.3, 109.6, 109.2, 103.6, 23.8, 23.1, 8.6, 7.3; $^{13}$C NMR signals for carboxyl group were not observed or very-low-intensity maybe owing to the long relaxation times of these carbon nuclei, $\delta_C$ of carboxyl group was 174.1 in published data. The 1H NMR and $^{13}$C NMR data were comparable to published data. HRESIMS m/z 345.0972 $[M-H]^-$ (calcd. for $C_{18}H_{17}O_7$, 345.0974); the MS/MS spectrum is deposited in the GNPS spectral library.

13-2: Proatranorin I (Compound 2)

$^1$H NMR (400 MHz, $CDCl_3$): $\delta_H$ 11.90 (s, OH), 11.70 (s, OH), 6.50 (s, 1H), 6.29 (s, 1H), 3.96 (s, 3H), 2.60 (s, 3H), 2.52 (s, 3H), 2.12 (s, 3H), 2.07 (s, 3H); $^{13}$C NMR (100 MHz, $CDCl_3$): $\delta_C$ 172.4, 170.3, 164.2, 162.9, 159.0, 152.6, 140.7, 139.8, 117.0, 116.4, 111.2, 110.1, 109.0, 104.2, 52.3, 24.6, 24.1, 9.4, 7.7; 1H NMR (400 MHz, $CDCl_3$) data was comparable to published data; $^{13}$C NMR (100 MHz, $CDCl_3$) data was comparable to 4-O-demethylbarbatic acid (Compound 1) data, except that there was one more oxygen-methyl carbon ($\delta_C$ 52.3) in compound 2. HRESIMS m/z 359.1132 $[M-H]^-$ (calcd. for $C_{19}H_{19}O_7$, 359.1131); the MS/MS spectrum is deposited in the GNPS spectral library.

13-3: Proatranorin III (Compound 4)

$^1H$ NMR (400 MHz, $CDCl_3$): $\delta_H$ 12.54 (s, OH), 12.45 (s, OH), 11.77 (s, OH), 10.35 (s, CHO), 6.54 (s, 1H), 6.40 (s, 1H), 2.68 (s, 3H), 2.59 (s, 3H), 2.08 (s, 3H); 1H NMR (400 MHz, $CDCl_3$) data was comparable to published data of atranorin (Compound 5), except that there was missing a methyl group ($\delta_H$ 3.99) at the carboxyl group in (Compound 4). HRESIMS m/z 359.0771 $[M-H]^-$ (calcd. for C18H15O8, 359.0767); the MS/MS spectrum is deposited in the GNPS spectral library.

Example 14: PKS Families in the Genus *Cladonia*

Example 14-1: PKS families in *Cladonia* spp. Forty-five gene cluster families (GCFs) including at least one iterative type I PKS gene were identified, using the Big-SCAPE program. Biosynthetic gene clusters (BGCs) of PKS1, PKS2, PKS4, PKS5, PKS15 and PKS16 families were conserved in the six *Cladonia* species plus *S. alpinum*, and BGCs of PKS3 and PKS10 families were conserved in the six *Cladonia* species. Previously, Timsina et al. identified thirteen PKS families conserved in species in the *Cladonia chlorophaea* species complex (PKS1, PKS2, PKS3, PKS5, PKS7, PKS10, PKS11, PKS12, PKS13, PKS14, PKS15, PKS16 and MSAS). The present inventors also identified these PKS families in our gene cluster network analysis (FIG. 2A). However, the present inventors failed to detect PKS12 homologs in the genomes of the six *Cladonia* species, even in the *C. grayi* genome from which the PKS12 family was originally identified. Three PKSs are manually detected and linked to respective PKS families, as the gene annotations were incomplete and fragmented so that the antiSMASH program failed to detect BGCs harboring the three PKSs: Cma06514 (PKS3), Cgr07347 (PKS10), and Cuc08442 (PKS19).

Example 15: Genetic Dereplication of *Cladonia* BGCs (Biosynthetic Gene Clusters)

To link unknown biosynthetic gene clusters in the six *Cladonia* spp. and *S. alpinum* to known compounds in other fungi, GCFs predicted by the Big-SCAPE program were coupled to previously characterized BGCs deposited in the MIBiG (Minimal Information about a Biosynthetic Gene cluster) database (v.1.4). As a result, eight GCFs and seven singleton BGCs were linked to known BGCs found in non-lichenized fungi (FIG. 2A). These conserved biosynthetic gene clusters (BGCs) in phylogenetically distant species suggested shared ancestries of the biosynthetic pathways between lichens and non-lichenized fungi. Nevertheless, these conserved BGCs exhibited a high degree of gene content variation, suggesting divergent pathways that may have led to chemical diversity. There were three lichen BGCs listed in the MIBiG database: BGCs for PKS8 in *C. uncialis*, PKS14 in *C. uncialis*, and PKS16 in *C. grayi*, which were indicated by dashed red circles in FIG. 2A.

Example 15-1: PKS8

The PKS8, also known as methylphloroacetophenone synthase (MPAS) in *C. uncialis*, is known to be involved in biosynthesis of usnic acid, based on phylogenetic analysis and gene expression study. A GCF of the PKS8/MPAS family is shared by *C. borealis, C. metacorallifera, C. rangiferina*, and *C. uncialis*. However, among these four *Cladonia* species, usnic acid has not been detected in *C. rangiferina*.

Example 15-2: PKS14

The putative 6-hydroxymellein BGC found in *C. uncialis* (BGC0001489) formed a GCF with PKS14 BGCs in *C. borealis* and *C. grayi*. The roles of the gene members of the 6-hydroxymellein BGC were tentatively assigned based on the terrein biosynthetic pathway, in which terA and terB act in concert to biosynthesize 6-hydroxymellein in *A. terreus*. In the present inventor's network analysis, the terrein BGC (MIBiG accession: BGC0000161) was not linked to the 6-hydroxymellein BGCs in the three *Cladonia* species, likely due to gene content variation observed between them; only three genes (terA, terB and terD) among the eleven gene members of the terrein BGC in *A. terreus* were conserved in the 6-hydroxymellein BGCs in the three *Cladonia* species.

Example 15-3: PKS13 및 PKS15

BGCs of the PKS15 family conserved in the six *Cladonia* spp. and *S. alpinum* were linked to many previously characterized BGCs including a 1,3,6,8-tetrahy-droxynaphthalene (T4HN) synthase responsible for melanin production in diverse fungi. For brevity, FIG. 2A showed only one BGC containing a T4HN synthase (BGC0001257) connected to the BGCs of the PKS15 family. The present inventors identified that PKS13 BGCs were also connected to known BGCs containing a T4HN synthase. Unlike the PKS15 family conserved in the six *Cladonia* spp. and *S. alpinum*, the PKS13 family was not found in *C. uncialis* and *S. alpinum*, showing 51-54% protein sequence identity with ElcPKS1 responsible for the melanin production in *Exophiala lecanii-corni*. The ElcPKS1 and PKS13 family formed a highly supported clade (bootstrap value of 99%) distinct from the PKS15 family and other conventional T4HNs, indicating that some *Cladonia* species possess two copies of melanin PKSs of different origin.

Example 15-4: PKS16

The putative grayanic BGC found in *C. grayi* (BGC0001266) is conserved in the six *Cladonia* spp. and *S. alpinum*. The PKS16 BGC was proposed to produce orsellinic acid-derived grayanic acid (a depsidone) that is found in *C. grayi*.

Example 15-5: PKS17

A GCF of the PKS17 family, shared by *C. borealis, C. macilenta* and *C. metacorallifera*, was linked to a BGC (BGC0001583) for the biosynthesis of emodin, an anthraquinone produced by many different fungi. In addition to the four core enzymes (an NR-PKS, metallo-β-lactamase, decarboxylase and anthrone oxygenase) that are necessary and sufficient for emodin biosynthesis, a few more tailoring enzymes including a cytochrome P450 monooxygenase were found in the homologous *Cladonia* BGCs. The P450 monooxygenase showed 39% sequence identity with the ClaM that mediates the coupling of two emodin derivatives in *Cladosporium fulvum*, suggesting that the P450 enzyme may be involved in biosynthesis of skyrin. Intriguingly, another BGC harboring the four core genes for emodin biosynthesis was found in the genome of *C. macilenta*, although in different arrangement with the PKS17 BGCs. This second BGC in *C. macilenta* for putative emodin biosynthesis formed a GCF with the PKS18 BGC in *C. uncialis*, which was homologous to the BGC of pestheic acid, an emodin derivative, found in *Pestalotiopsis fici*.

Example 15-6: PKS34

A GCF of the PKS34 family shared by *C. macilenta* and *C. metacorallifera* was linked to a BGC (BGC0001242) for the biosynthesis of fusarubin, the red mycelial pigment produced by *Fusarium fujikuroi*. However, the BGC contents were highly variable; only putative homologs of fsr1 (encoding an NR-PKS), fsr4 (encoding an alcohol dehydrogenase) and fsr5 (encoding a short-chain dehydrogenase) in the fusarubin BGC can be found in the PKS34 BGCs.

Example 15-7: PKS37

The patulin BGC (BGC0000120) in *Penicillium expansum* was connected to a GCF of the PKS37 family shared by *C. borealis, C. metacorallifera* and *C. uncialis*. Among the 15 gene members of the patulin BGC, ten genes homologous to patF-patO can be found in the three *Cladonia* spp. (except for patF in *C. borealis*), which are necessary for the biosynthesis of neopatulin, the immediate precursor of patulin. Homologs of patD and patE responsible for the final conversion of neopatulin to patulin were absent in the *Cladonia* genomes. Instead, other tailoring enzymes found were an epimerase in *C. metacorallifera* and *C. uncialis*, a TauD-like dioxygenase in *C. borealis* and *C. uncialis*, and two short chain dehydrogenases in *C. uncialis*.

BGC Example 16: Singleton BGCs Connected to the MIBiG Database

Several previously characterized BGCs were connected to BGCs found in a single species (singleton BGCs). These singleton BGCs tend to exhibit little gene content variation and high sequence similarity to corresponding BGCs found in non-lichenized fungi, suggesting recent introductions of these BGCs into lichens. These likely horizontally transferred BGCs from non-lichenized fungi were as follows: the sorbicillin BGC (BGC0001404) linked to a BGC in *C. macilenta*, the terreic acid BGC (BGC0000160) linked to a BGC in *C. grayi*, the hypothemycin BGC (BGC0000076) linked to a BGC in *C. rangiferina*, the curvupallides BGC (BGC0001563) linked to a BGC in *C. uncialis*, and the depudecin BGC (BGC0000046) linked to a BGC in *S. alpinum*. The monascorubrin BGC (BGC0000099) and betaenones BGC (BGC0001264) were also connected to BGCs in *C. uncialis* in the present inventors' network analysis, as well as in an earlier study on homology mapping of *C. uncialis* PKSs.

Example 17: Notes on Homology Mapping of *Cladonia* PKS Families

Example 17-1: Homology Mapping of Conserved Lichen PKS Families

Although gene cluster network analysis ascribed many lichen BGCs to known compounds with high likelihood, there may be more homologous BGCs that were not connected to previously characterized BGCs in non-lichenized fungi, due to high gene content variations. Therefore, the present inventors performed BLAST searches of 45 PKS families against the NCBI non-redundant protein sequences database to identify *Cladonia* PKS families homologous to PKS genes with known compounds.

Example 17-2: PKS4

The PKS4 family encodes an R-PKS enzyme conserved in the six *Cladonia* spp. and *S. alpinum*. The PKS4 family can be found in lichenized and non-lichenized fungi and appears to have undergone co-evolution with the physically-associated type III PKS.

Example 17-3: PKS5

The PKS5 family was conserved in the six *Cladonia* spp. and *S. alpinum*, encoding a PKS-NRPS hybrid enzyme that showed a high sequence similarity to the xenolozoyenone PKS in *Glarea lozoyensis* (56% at protein sequence level). Homologs of the PKS5 family can be found in diverse fungi. Interestingly, two tandem genes encoding R-PKS and NRPS enzymes for the xenolozoyenone biosynthesis in *G. lozoyensis* are co-transcribed into one dicistronic mRNA under the control of the same promoter. Thus, it needs to be examined whether the PKS5 family in lichens also encodes two separate polypeptides for R-PKS and NRPS enzymes or a single peptide for a PKS-NRPS hybrid enzyme.

Example 17-4: PKS9

The PKS9 family was shared by *C. borealis, C. macilenta, C. metacorallifera* and *C. uncialis*, which is similar to an NR-PKS (MpaC) responsible for the biosynthesis of mycophenolic acid derived from 5-methylorsellinic acid in *Penicillium brevicompactum* (44% protein sequence identity), as described in a previous homology mapping study. Also, the PKS9 family showed 43-45% protein sequence identity to NR-PKSs (AdrD, AndM, AusA, NvfA, PrhL and Trt4) involved in the biosynthesis of meroterpenoids derived from 3,5-dimethylorsellinic acid in *Aspergillus* and *Penicillium* species. However, the PKS9 BGCs in the *Cladonia* genomes lacked biosynthetic genes related to terpene biosynthesis, such as prenyltransferase and terpene cyclase.

Example 17-5: PKS18

The PKS18 family shared by in *C. macilenta* and *C. uncialis* showed 64-68% protein sequence identity to an NR-PKS (PtaA) involved in the biosynthesis of pestheic acid, an emodin derivative, in *Pestalotiopsis fici*, as described in a previous homology mapping study.

Example 17-6: PKS21

A purple pigment biruloquinone was first discovered in a foliose lichen *Parmelia birulae*. Although biruloquinone has not been found in *Cladonia* species in nature, the present inventors previously identified a chemical variant of the genome-sequenced mycobiont isolated from *C. macilenta*, producing biruloquinone in axenic culture. The present inventors tentatively assigned the PKS21 family to the biosynthesis of biruloquinone by the whole-transcriptome comparison between the biruloquinone producer and non-producer.

Example 17-7: PKS22

A red pigment cristazarin, a naphthazarin derivative, was originally identified from a mycobiont culture of *C. cris-*

*tatella*. The present inventors established an optimum culture condition for cristazarin production in a mycobiont isolated from the genome-sequenced *C. metacorallifera* and ascribed the PKS22 family to the biosynthesis of cristazarin, based on the observation that the PKS23 was highly upregulated in cristazarin-inducing conditions in *C. metacorallifera*.

Example 17-8: PKS24

The PKS24 family was shared by *C. borealis, C. macilenta, C. metacorallifera* and *S. alpinum*. The PKS24 BGC in *C. metacorallifera* was slightly different from the ones in the other three species, with a fragmented PKS24 gene. The PKS24 family formed a monophyletic clade maximally supported by 100% bootstrap with FgPKS14 involved in orsellinic acid biosynthesis in *Fusarium graminearum*, showing 46-48% protein sequence identity to FgPKS14.

Example 17-9: PKS30

The PKS30 family showed 52-53% protein sequence identity to an NR-PKS (wA) responsible for the biosynthesis of the conidial yellow pigment (aka. YWA1), a naphthopyrone produced by *A. nidulans*. The PKS30 BGCs conserved in *C. borealis, C. macilenta, C. metacorallifera* and *C. uncialis* are likely involved in the biosynthesis of the red apothecial pigment, rhodocladonic acid, albeit the pigment has not been detected in *C. uncialis*. There were only two GCFs (the PKS21 and PKS30 families) shared by the three red apothecial pigment producers, *C. borealis, C. macilenta* and *C. metacorallifera*. The PKS21 and PKS30 families belong to the NR-PKS Groups III and IV, respectively, which include NR-PKSs involved in the biosynthesis of naphthopyrone-derived compounds. Since the PKS21 family was tentatively assigned to the biosynthesis of biruloquinone (a phenanthrenequinone), the PKS30 family is the last remaining naphthopyrone PKSs shared by the three red apothecial pigment producers. This putative assignment was strengthened by the presence of enzymes necessary for the biosynthesis of rhodocladonic acid, such as O-methyltransferase and two monooxygenases in the PKS30 BGCs. A proposed biosynthetic pathway for rhodocladonic acid from a naphthopyrone precursor was shown below.

Example 17-10: PkeA

BGCs shared by *C. borealis* and *C. metacorallifera* included an NR-PKS showing 63-65% protein sequence identity to PKeA (also known as DbaI) responsible for the biosynthesis of felinones in *A. nidulans*. The present inventors refrained from assigning a PKS family number for the NR-PKSs homologous to PkeA/DbaI, as these PKS genes appear to have arisen through horizontal transfer and may be specific to a certain lineage of *Cladonia*, as with the other *Cladonia* NR-PKSs that belong to the Group VII (e.g., sorbicillin BGC in *C. macilenta*).

Example 18: Metabolic Potentials of Lichen

Figure 1:
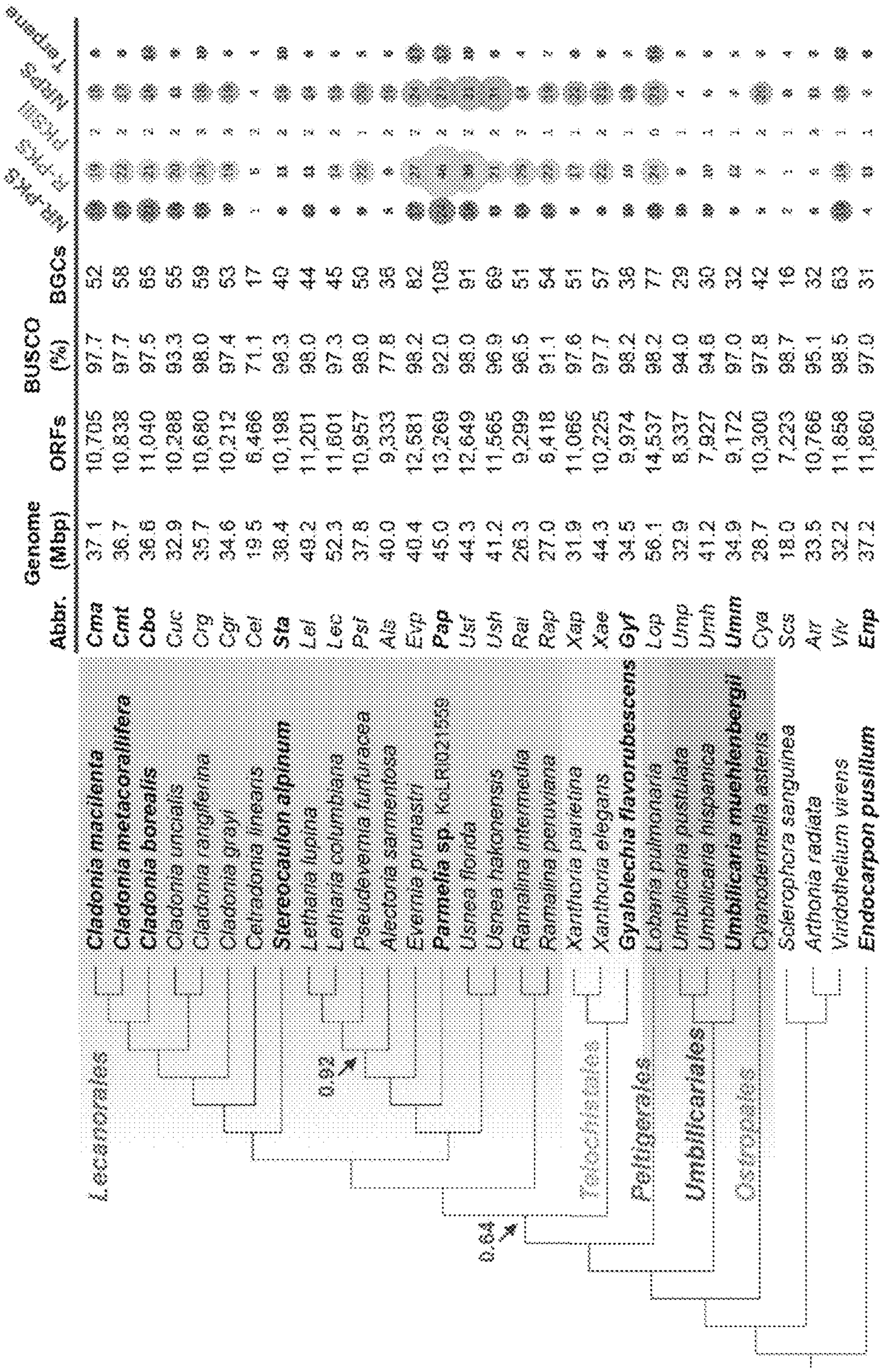
FIG. 1 shows the genome-encoded metabolic potentials of lichen. A coalescent-based species tree is reconstructed for 29 lichen-forming fungi and *Cyanodermella asteris* (a plant endophyte). The tree is rooted to *Endocarpon pusillum*. All local posterior probabilities for nodal supports are higher than 0.98, except those marked by arrows. The five orders of the Lecanoromycetes are highlighted with different colors, and lichen genomes sequenced by Korean Lichen Research Institute are marked in bold. BUSCO describes the completeness of the genome's assemblies. The number of biosynthetic gene clusters (BGCs) are predicted by antiSMASH, and bubble plots indicate relative abundance of core biosynthetic enzyme categories: NR-PKS, non-reducing type I PKS; R-PKS, reducing type I PKS (including PKS-NRPS hybrid enzymes); PKSIII, type III PKS; NRPS, nonribosomal peptide synthetase (including NRPS-like enzymes); and Terpene, biosynthetic enzymes related to terpenoids production.
Figure 5:
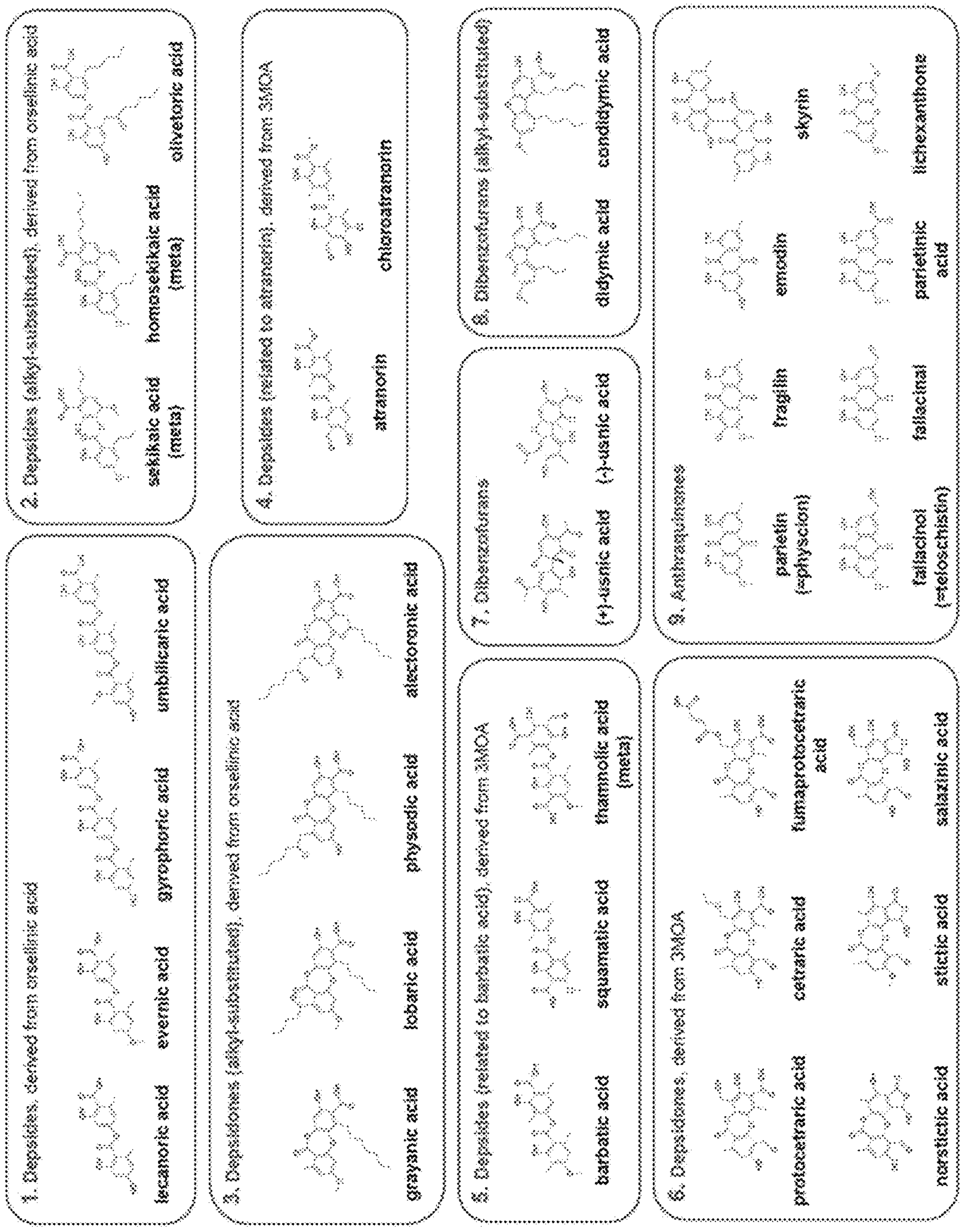
FIG. 5 shows chemical structures of cortical and medullary substances of lichens. Lichen substances reported in the 30 genome-sequenced species are grouped by nine chemical groups, based on the chemical structures (Also, see Table 2). Here, 3MOA is an abbreviation for 3-methylorsellinic acid.

To examine evolutionary relationships of LFF and compare their genome-encoded metabolic potentials, a coalescent-based tree of 393 single-copy orthologous genes was reconstructed, using eight genomes that we have sequenced and 22 genome assemblies available in the NCBI database and JGI website, as of September 2020. A majority of the sequenced species (26 out of 30) belong to the Lecanoromycetes and four LFF were placed outside of the Lecanoromycetes: *Arthonia radiata* (Arthoniomycetes), *Endocarpon pusillum* (Eurotiomycetes), *Sclerophora sanguinea* (Coniocybomycetes) and *Viridothelium virens* (Dothideomycetes). Barring the genomes of *Alectoria sarmentosa* and *Cetradonia linearis*, completeness of the genomes assessed by BUSCO analysis was greater than 91% (FIG. 1). An endangered lichen *Ce. linearis* and *Sc. sanguinea* had compact genomes shorter than 20 Mbp (FIG. 1). Except for these two species, all genomes were 26.3-56.1 Mbp in size, containing 7,927-14,537 open reading frames (FIG. 1). Genome-encoded metabolic potentials of the 30 species were investigated by mining the genomes for BGCs using antiSMASH. Metabolic potentials of the sequenced LFF were highly variable, with BGC counts of 16-108 (FIG. 1); *Parmelia* sp. KoLRI021559 showed the greatest BGC diversity, whereas the genomes of *Ce. linearis* and *Sc. sanguinea* carried the smallest sets of BGCs which may be attributable to their contracted genome size. Notably, the six *Cladonia* genomes possess 52-65 BGCs and encode similar numbers of PKSs; an average of 16 NR-PKSs and 20 reducing type PKS (R-PKS) (FIG. 1). The six *Cladonia* spp. produce unique sets of SMs of polyketide origin (see Table 2 and FIG. 5), which make it ideal for studying inter-species PKS gene diversity and identifying BGCs responsible for biosynthesis of cortical or medullary substances of lichens through comparative analysis.

Table 2 below summarizes the lichen materials reported in the genome-sequence analysis of 30 species.

TABLE 2

| speices | Lichen substances |
|---|---|
| *Cladonia macilenta* | barbatic acid, didymic acid |
| *Cladonia metacorallifera* | thamnolic acid), **usnic acid**, didymic acid |
| *Cladonia borealis* | barbatic acid, **usnic acid** |
| *Cladonia uncialis* | squamatic acid, **usnic acid** |
| *Cladonia rangiferina* | **atranorin**, fumaprotocetraric acid |
| *Cladonia grayi* | grayanic acid, fumaprotocetraric acid |
| *Cetradonia linearis* | — |
| *Stereocaulon alpinum* | lobaric acid, **atranorin**, stictic acid |
| *Letharia lupina* | **atranorin**, norstictic acid |
| *Letharia columbiana* | **atranorin** |
| *Pseudevernia furfuracea* | olivetoric acid, physodic acid, **atranorin/chloroatranorin** |
| *Alectoria sarmentosa* | alectoronic acid, **usnic acid** |
| *Evernia prunastri* | lecanoric acid/evernic acid, physodic acid, **atranorin/chloroatranorin**, salazinic acid, **usnic acid** |
| *Parmelia* sp. KoRLI021559 | **atranorin/chloroatranorin**, salazinic acid |
| *Usnea florida* | thamnolic acid, norstictic acid/salazinic acid, **usnic acid** |
| *Usnea hakonensis* | **usnic acid** |
| *Ramalina intermedia* | sekikaic acid, atranorin, **usnic acid** |
| *Ramalina peruviana* | sekikaic acid, **usnic acid** |
| *Xanthoria parietina* | **parietin**/fallacinol/parietinic acid/emodin |
| *Xanthoria elegans* | **parietin** |
| *Gyalolechia flavorubescens* | **parietin**/fallacinol/fragilin/emodin |
| *Lobaria pulmonaria* | gyrophoric acid, atranorin, norstictic acid/salazinic acid |
| *Umbilicaria pustulata* | lecanoric acid/gyrophoric acid/umbilicaric acid, skyrin |
| *Umbilicaria hispanica* | lecanoric acid/gyrophoric acid/umbilicaric acid, skyrin |
| *Umbilicaria muehlenbergii* | lecanoric acid/gyrophoric acid |
| *Cyanodermella asteris* | skyrin |
| *Sclerophora sanguinea* | — |
| *Arthonia radiata* | Not detected |
| *Viridothelium virens* | **lichexanthone** |
| *Endocarpon pusillum* | — |

Example 19: Genetic Dereplication of *Cladonia* PKSs

To search for PKS genes involved in biosynthesis of lichen polyketides, namely depside and depsidone series compounds, the present inventors focused on 226 BGCs harboring at least one PKS in the six *Cladonia* spp. plus a related Antarctic lichen *S. alpinum*, from which a total of 242 PKSs were identified. The present inventors first conducted clustering analysis of the conserved ketosynthase (KS) domains of each PKS and identified a number of clusters that are suggestive of homologous relationships. Twelve PKS families described in an earlier study on the *Cladonia chlorophaea* species complex were also detected in our clustering analysis, indicating that a significant proportion of PKS genes are conserved in the genus *Cladonia*. However, little is known about their products. Therefore, the present inventors linked BGCs to known compounds in non-lichenized fungi, using the Big-SCAPE program that maps BGC diversity onto sequence similarity networks. The network analysis was used to graphically summarize three attributes of BGCs: (i) PKS families associated with the network (numbers), (ii) species distribution across the network (nodes), and (iii) degrees of similarity between pairs of BGCs (edges) (FIG. 2A). As depicted by the gene cluster network, the BGCs harboring at least one PKS gene were grouped into 45 gene cluster families (GCFs). Eight GCFs and seven species-specific BGCs (labelled in red) were coupled to previously characterized BGCs deposited in the MIBiG database. FIG. 2B summarized phyletic distribution of *Cladonia* PKS families, denoting signature SMs linked to *Cladonia* PKS families.

Example 20: Identification of Putative Atranorin BGC

Figure 2:
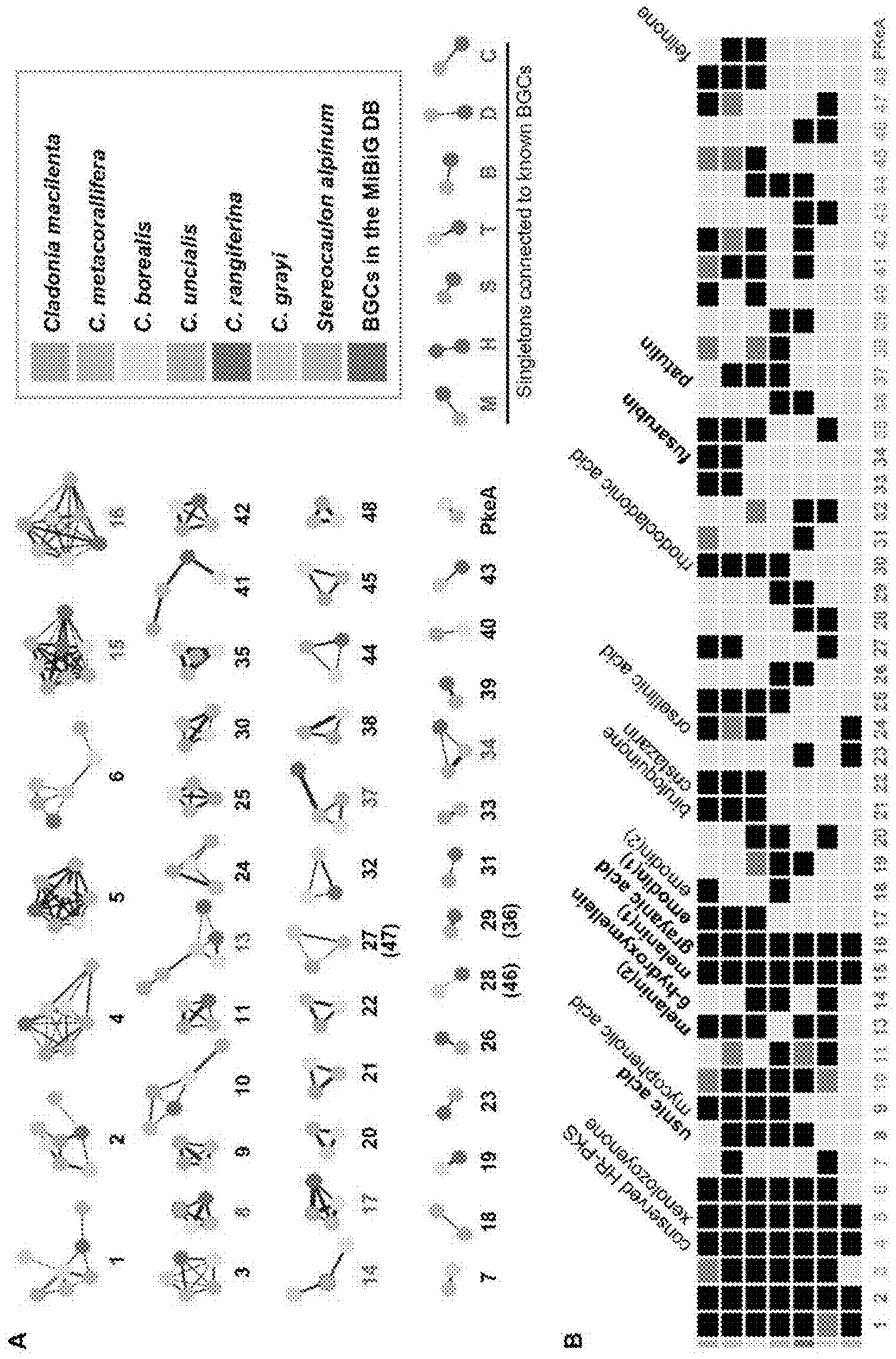
FIG. 2 shows Polyketide BGC diversity in *Cladonia* species. (A) Forty-five gene cluster families (GCFs) were identified by gene cluster network analysis in the six *Cladonia* spp. And *Stereocaulon alpinum*. GCFs are labelled with their associated PKS families. Numbers in red indicate PKS families connected to characterized BGCs deposited in the MIBiG database. Nodes indicate BGCs and are color-coded by species (see the inset). Nodes enclosed by a red dashed circle in the PKS8, PKS14 and PKS16 subnetworks are lichen BGCs in the MIBiG database. Edge width was drawn proportional to squared similarity between a pair of BGCs. Singleton BGCs that connected to known BGCs are labelled as follows: M, monascorubrin BGC; H, hypothemycin BGC; S, sorbicillin BGC; T, terreic acid BGC; B, betaenones BGC; D, depudecin BGC; C, curvupallides BGC. (B) Phyletic distribution of PKS families evidenced by gene cluster network analysis. Numbers in violet and ochre indicate NR-PKS and R-PKS families, respectively. Black squares indicate the presence of PKS families, and grey squares indicate pseudogenes or partial genes due to incomplete gene annotation. Signature secondary metabolites linked to *Cladonia* PKS families by genetic dereplication are marked in bold.

The gene cluster network analysis in the six *Cladonia* spp. and *S. alpinum* revealed that the PKS23 family among the 45 GCFs may be involved in biosynthesis of atranorin, the major cortical substance of diverse macrolichens, as it was the sole GCF shared by the two atranorin producers, *C. rangiferina* and *S. alpinum* (FIG. 2). Atranorin is unique in its structure having a methoxycarbonyl group within the 3MOA moiety, which is rarely found in other depsides and depsidones series compounds. A BLAST search with an O-methyltransferase (OMT) in the PKS23 BGC in *C. rangiferina* showed 37% protein sequence identity to the Trt5 (UniProtKB:Q0C8A3), an OMT that mediate the formation of a methoxycarbonyl group within the 3,5-dimethylorsellinic acid moiety in *A. terreus* during the biosynthesis of terretonin (a meroterpenoid) (Table 3).

Table 3 below summarizes the information on the PKS23 biosynthetic gene cluster of *Cladonia rangiferina*.

TABLE 3

| ORFa (Crg) | Size (aa) | BLASTP homolog[b] | Identity (%) | Conserved domain | E-value |
|---|---|---|---|---|---|
| 06811 | 744 | MFS monosaccharide transporter | 71 | Sugar transporter (Pfam00083) | 1e−105 |
| 06812 | 306 | export control protein) CHS7-like | 68 | chitin synthase III catalytic subunit (Pfam12271) | 1e−131 |
| 06813 | 495 | TFIIH complex p47 subunit | 58 | TFIIH complex subunit Ssl1-like (Pfam04056) | 1e−82 |
| **06814** | 549 | MES multidrug transporter (**atr4**) | 50 | major facilitator superfamily (Pfam07690) | 9e−31 |
| **06815** | 346 | Trt5, O-methyl-transferase (**atr3**) | 37 | SAM- dependent methyltransferase (Pfam08241) | 1e−04 |
| **06816** | 508 | Cytochrome P450 monooxygenase (**atr2**) | 43 | Cytochrome P450 (Pfam00067) | 3e−57 |
| **06817** | 2,513 | non-reducing polyketide synthase (**atr1**) | 44 | SAT-KS-AT-PT-ACP-MT-TE | |
| 06818 | 472 | hypothetical protein | 33 | phospho-transferase enzyme family (Pfam01636) | 4e−08 |
| 06819 | 2,377 | reducing polyketide synthase (R-PKS) | 40 | KS-AT-DH-ER-KR-ACP | |
| 06820 | 184 | hypothetical protein | 40 | domain of unknown function, DUF3237 (Pfam11578) | 5e−22 |
| 06821 | 301 | hypothetical protein | 34 | domain of unknown function, DUF2306 (Pfam10067) | 2e−09 |
| 06822 | 236 | hypothetical protein | 28 | (not detected) | |
| 06823 | 356 | hypothetical protein | 32 | (not detected) | |
| 06824 | 565 | putative dimethylaniline monooxygenase | 41 | flavin-binding monooxygenase-like (Pfam00743) | 3e−14 |

aORF: Open reading frame of *C. rangiferina*); the synthetic core genes are highlighted in.

[b]For BLAST searches, the NCBI non-redundant protein sequence database for four *Aspergillus* species is used: *Aspergillus fumigatus* (taxid: 746128), *A. nidulans* (taxid: 162425), *A. niger* (taxid: 5061), and *A. terreus* (taxid: 33178).

Figure 3:
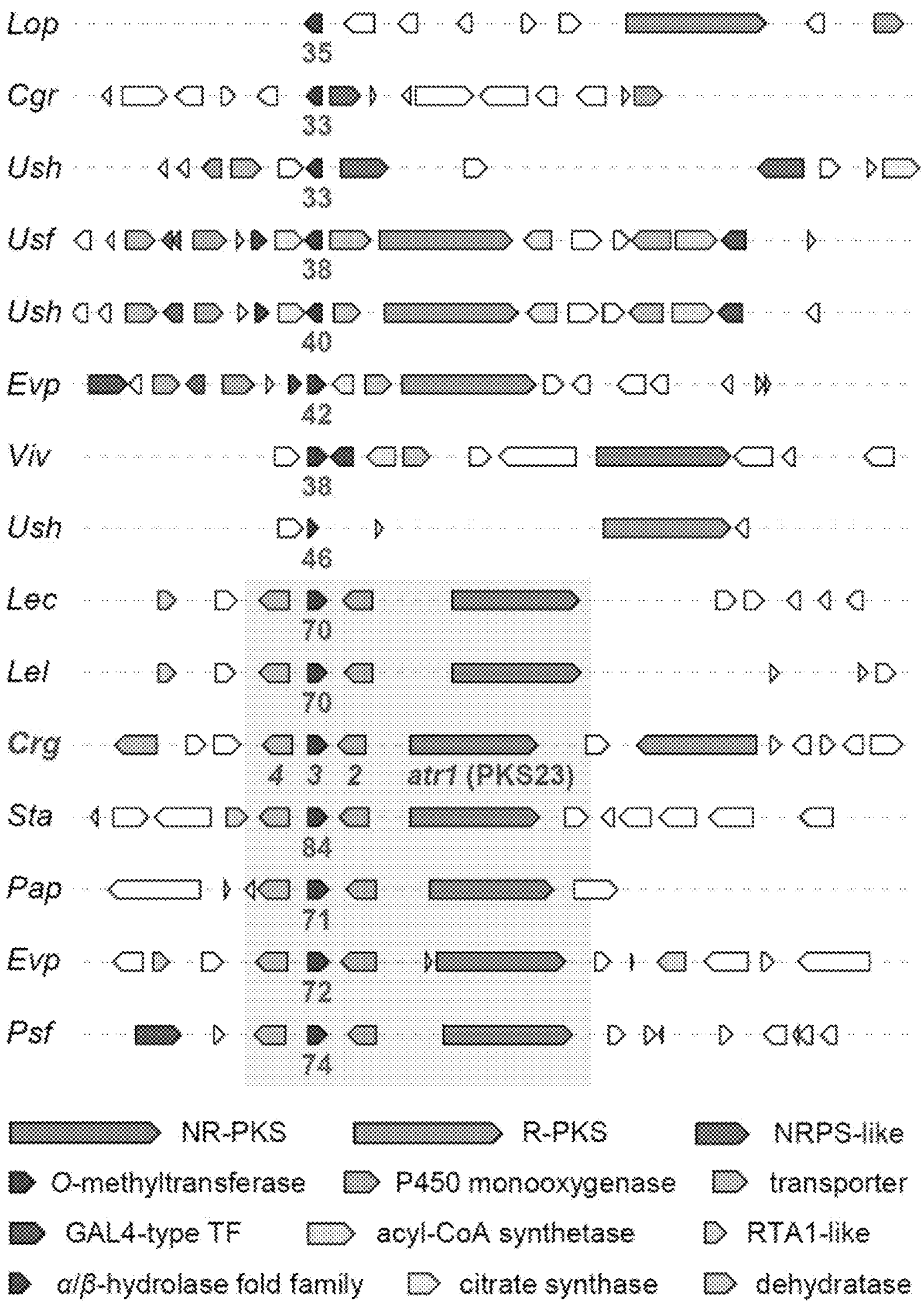
FIG. 3 shows an organization of putative atranorin BGCs. Fifteen BGCs including an O-methyltransferase that shows significant hits to the one in the PKS23 BGC in *C. rangiferina* (Crg, labeled in red) are identified from 1,527 BGCs detected in the 30 genomes, using the CORASON analysis pipeline. Lichen species that harbor the BGCs are labelled with their abbreviated names, as in FIG. 1. Numbers in blue indicate percent protein sequence identity of homologous OMTs to the one in Crg. Among the 15 BGCs, seven BGCs harbor four synthetic genes (shaded box): atr1 (PKS23), atr2, atr3 and atr4. Genes related to secondary metabolism are color-coded, based on their predicted function. NR-PKS, non-reducing type I PKS; R-PKS, reducing type I PRS; NRPS, nonribosomal peptide synthetase; TF, transcription factor; RTA, resistance to 7-aminocholesterol.

To examine presence of conversed PKS23 BGCs in other lichens that produce atranorin, the present inventors adopted the CORASON pipeline that is useful for studying conservation and variation of BGCs within and across GCFs. The protein sequence of the OMT in the PKS23 BGC in *C. rangiferina* was queried against a total of 1,527 BGCs detected in the 30 genomes. The present inventors identified 15 BGCs each harboring an OMT that showed a significant hit (>33% protein sequence identity) (FIG. 3). Among the 15 BGCs, seven BGCs contained four synthetic core genes: PKS23 (coined atr1), a cytochrome P450 monooxygenase (atr2), an OMT (atr3) and a transporter (atr4) (FIG. 3 and Table 3). These syntenic BGCs were exclusively found in the atranorin-producing lichens among the 30 sequenced species (see Table 2).

Example 21: Reconstruction of Atranorin Biosynthetic Pathway

Figure 6:
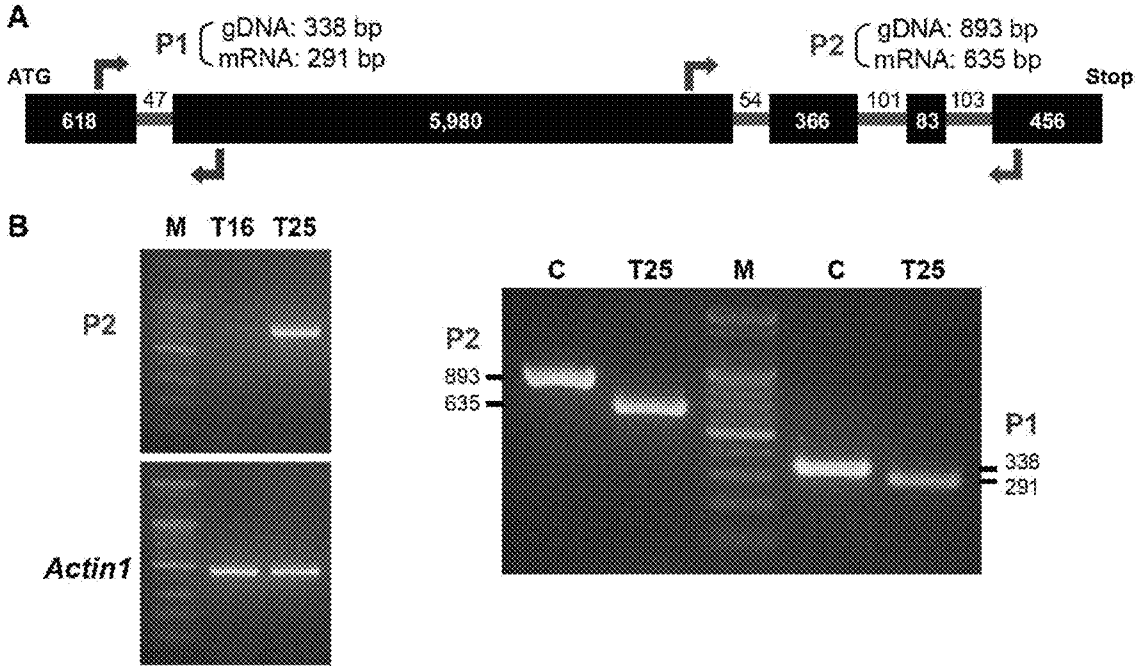
FIG. 6 shows the results of verification of heterologous expression of PKS23. (A) A schematic diagram of the PKS23 (atr1) gene structure in *Stereocaulon alpinum*. Black boxes are exons, and grey lines are introns. The numbers indicate the size of exons and introns in base pairs (bp). P1 and P2 are primer pairs used in RT-PCR analyses. These primer pairs are designed to include one or more intron regions so that mRNA expression can be distinguished from genomic DNA (gDNA) amplification. (B) RT-PCR analyses of two putative transformants (T16 and T25) carrying the plasmid sol1::atr1/pDS35. No band corresponding to gDNA amplicon for Actin1 reference gene (633 bp; cf. 482 bp for mRNA) is observed, indicating that there was no genomic DNA contamination (lower left panel). The transformant T25 shows stronger expression of the introduced atr1 than the transformant T16 (upper left panel). Splicing of the four introns in the atr1 is confirmed by comparison of band sizes between the plasmid sol1::atr1/pDS35 (C) and RNA sample (T25), using P1 and P2 primer pairs. The expected band sizes for mRNA expression and plasmid DNA amplification are indicated by numbers to left and right sides of the gel image in bp. Here, M is a 100 bp DNA ladder.

Despite arduous efforts made for heterologous expression of lichen PKS genes in well-established heterologous hosts, such as *A. nidulans* and *A. oryzae*, the attempts were unsuccessful for yet-unknown reasons (11, 23). Thus, the present inventors set out to establish a new heterologous expression system, using a plant pathogenic fungus *Ascochyta rabiei* (Dothideomycetes). On the basis of the chemical structure and the predicted functions of three biosynthetic genes in putative atranorin BGCs, a polyketide pathway for atranorin can be envisioned (FIG. 4A). To investigate the roles of individual genes, the present inventors first generated a "clean host" that showed no appreciable metabolite production by removing the BGC for biosynthesis of solanapyrones from the wild-type *As. rabiei* (FIG. 4B). Then, the present inventors introduced the atr1 cloned from the *S. alpinum* gDNA into the "clean host". Expression and correct intron splicing of the atr1 were confirmed by RT-PCR analyses (see FIG. 6). The LC-MS/MS and NMR analyses indicated a known lichen depside, 4-O-demethylbarbatic acid (Compound 1) was produced by a strain expressing the atr1 (FIGS. 4B and 4C), suggesting that two 3MOA units were joined into a depside by the Atr1 itself.

As the biosynthesis of atranorin from compound 1 requires oxidation of a methyl group and methylation of the carboxyl group within each of the two 3MOA units (FIG. 4A), the present inventors individually introduced genes encoding the atr2 and the atr3 to the atr1-expressing strain. Co-expression of the atr1 with the atr3 yielded 7'-O-methylated analogue of compound 1, proatranorin I (Compound 2), indicating that the Atr3 is indeed a carboxyl methylase, as is the Trt5 in *A. terreus* (FIGS. 4B and 4C). The LC-MS/MS analysis showed that co-expression of the atr1 with the atr2 yielded compounds 3 and 4, which were annotated as a hydroxylated analogue of compound 1 (proatranorin II) and a further oxidized aldehyde (proatranorin III), respectively (FIGS. 4B and 4C). NMR analysis on the isolated proatranorin III (Compound 4) confirmed that the oxidation by the Atr2 occurs at C-9 of compound 1. Finally, the present inventors generated a strain expressing the three genes, the atr1, atr2 and atr3. The production of atranorin (Compound 5) was confirmed by MS/MS spectral matching with the reference spectrum of atranorin in the Lichen Database. It was also confirmed by comparison of the chemical profile with an authentic voucher specimen for the sequenced *S. alpinum* that produces atranorin (compound 5) and lobaric acid, as a cortical and medullary substance, respectively (FIGS. 4B and 4C). Intriguingly, MS/MS spectral matching of compound 6 identified it as another lichen depside, baeomycesic acid, which has not been reported from *S. alpinum* in nature, suggesting that the Atr3 exhibits relaxed substrate specificity in the heterologous host.

Example 22: a Novel Phylogenetic Clade of PKS Responsible for Biosynthesis of Lichen Substances To study the evolutionary relationships of fungal NR-PKS and the Atr1 responsible for atranorin production, the present inventors reconstructed a phylogenetic tree of the concatenated sequences of conserved KS and product template (PT) domains of 103 NR-PKSs found in the six *Cladonia* spp. and *S. alpinum*, and 82 NR-PKSs that have been linked to known compounds in non-lichenized fungi. Fungal NR-PKSs were hitherto largely classified into eight groups (Groups I-VIII) in previous phylogenetic analyses (7, 8, 42-44). Here, the present inventors identified a novel NR-PKS group (Group IX) supported by 100% bootstrap, which contained the PKS23 family as well as the PKS1 and PKS2 families. The PKS1 family was previously proposed to biosynthesize 3MOA-derived lichen substances in *C. rangiferina*. For lichen NR-PKSs in the Group IX, all but the PKS2 in *S. alpinum* possessed a C-methyltransferase (cMT) domain involved in the methylation of polyketide intermediates. Intriguingly, the newly identified Group IX included three previously characterized NR-PKSs, AscC, StbA and TmPKS12, in non-lichenized fungi. These NR-PKSs lack cMT domain and are known to produce orsellinic acids. Moreover, it is noteworthy that the Group VIII basal to the Group IX included several NR-PKSs that have been linked to orsellinic acid-derived compounds in mushroom-forming fungi (Agaricomycetes) and *Fusarium graminearum*, indicating that the PKS1 and PKS2 families are likely involved in biosynthesis of lichen substances derived from a methylated form of orsellinic acid, as with the PKS23 family.

[Accession Number]

Depository institution: Korean Agricultural Culture Collection (KACC), National Institute of Agricultural Science, International Depositary Authority Depository address: 166 Nongsaengmyeong-ro, Iseo-myeon, Wanju-gun, Jeollabuk-do 55365, Republic of Korea Deposited biological material: *Ascochyta rabiei* ATR-11 strain Accession number: KACC 83048BP Date of original deposit: May 28, 2021

The invention claimed is:

1. A recombinant expression vector for producing a lichen-derived metabolite, comprising an atranorin biosynthesis gene selected from the group consisting of SEQ ID NO: 1, SEQ ID NO: 3, and SEQ ID NO: 5.

2. A recombinant microorganism transformed with the recombinant expression vector according to claim 1.

3. A method of producing a lichen-derived metabolite, comprising a step of culturing a recombinant microorganism transformed with a recombinant expression vector comprising an atranorin biosynthesis gene selected from the group consisting of SEQ ID NO: 1, SEQ ID NO: 3, and SEQ ID NO: 5, wherein the lichen-derived metabolite is one or more selected from the group consisting of 4-O-demethylbarbatic acid, proatranorin I, proatranorin II, proatranorin III, atranorin, and baeomycesic acid.

4. An *Ascochyta rabiei* ATR-11 strain (Accession Number: KACC 83048BP).

5. A method of producing atranorin, comprising a step of culturing the strain according to claim 4.

* * * * *

SEQUENCE LISTING

```
<160> NUMBER OF SEQ ID NOS: 46

<210> SEQ ID NO 1
<211> LENGTH: 7808
<212> TYPE: DNA
<213> ORGANISM: Artificial Sequence
<220> FEATURE:
<223> OTHER INFORMATION: Stereocaulon alpinum atr1 gene(MZ277879)

<400> SEQUENCE: 1

atggcgtcta accatgagga gctaccttca atggtagtgt tcagcccgca gagcaaagcc      60

ccaaaagaag gatacctcga tgagttacgg tcatatctat gcggcaaggc tgaacttcga     120

cctttgcttg atggtatcga aaaccttcca aacacctggt caatctttgc tcaaaggaac     180

tccgacattg cagctctgac tcaaggaatc cggtacacac aggcactctc agactgggcc     240

aagcatggaa cttcgtcagg aatctcgaac gttatgtctg ggatcctatc gttgcctctc     300

ttgaccatca ttcaggtggt ccaatacttc caattccttg aagtgaaaaa gctccgtcac     360
```

agcgacttca tggagcgact gaggtgtagg ggtggagttc aagggtattg tggcggccta 420
atgcctgcca ttgccatcgc ctgctctgcg acagaagctg aggttgttac caacgctgtt 480
aaagcgatgg gtattgcact aggtgttggc gcttacgggg agcttgggga cgatgagaac 540
gtcctagggc caactacaat agttgtccgc ctcaagcagg agggccaagg tggagacatc 600
ataaaggact ttcctgacgt gagctgctcg ttccgcacct accaaactca ctaactttgt 660
tacaggcgca tatatcagct atcacggacc caaagaccgt cagcattgta gggtcagccc 720
catctttggc agagatacaa gcccgagtga agtctaacgg catgcaaacc caagccatgc 780
atctgcgtgg gaaagtgcat aatcccgaaa acgctaatct agcgctggag ctttgcatgc 840
tttgcgacga gcatgaggaa ctctctttgc caaacgcttc acacttgacg gctcctttga 900
gatctaacaa gacagggaag aagttattag atgtctctct tactcatgaa gcgatcgaaa 960
caatcctggc atcctgctgt caatggtacg accttctcaa aggggtgtgc aaagacttgg 1020
agaaaacagg aactcaatca caccttttcg catcgttcgg cattggcgac tgcatccctc 1080
tgacaccgtt tcatcaggca gggctacaga ttaccaaatt ggacgttctc tcctttgtca 1140
aagccttgat gccgcctgtt ctaccaatgt ccggtcacaa ccaccaatat gcttatccaa 1200
ctgacgctgt ggctgtcgtc ggaatggcgt gtcgcctacc gggtgccaac agcgtcgaag 1260
aactctggga tctgatctcg tccggtggtt caactgttac ccctgtccca gaagatcgga 1320
tggatattgc aggtagcttt cgagctatgc aagatccgaa gtgggctgct aagcaacaat 1380
ggtggggcaa ttttatctct gatattgccg gatttgacca cagcttcttc cgcatgagcc 1440
ctcgggaagc cgcatcgatg gatccacaac aacgcattct cctcgagaca gcataccaag 1500
caatggagtc gagtggctac cttggttcgc atcgacgcga gtcaggtgat ccagtgggag 1560
tattcctagg agcaagtttc gtcgagtacc tggacaatac ttcctcaaac ccaccgacag 1620
catacacctc cactggcaca atcagggcgt ttttgagcgg caagataagt tattactttg 1680
gctggaccgg tccttctgaa attctcgaca cagcatgctc gtcgtctctg gttgccatta 1740
acagggcctg caaggcgatt cagaacgatg agtgccccat ggcacttgct ggtggcgtta 1800
atctaattac tggtatccac aattatttgg atctcgcaaa agcaggcttc cttagtccta 1860
gtggacaatg caagccgttt gatggcgctg ctgatggcta ctgccgttcg gaaggcgcgg 1920
gtctcgttgt tctcaagcgg ttgagccagg cattgaccga tgggaatcag atccttggcg 1980
tcatcacggg ggctagcacc aatcaaggcg gtttaagtcc atcgctcaca gtcccgcaca 2040
gcgctgccca ggtcaaattg taccaaaaca ttcttcatca ggcgggaatg agaccggagc 2100
aagtttctta ttgcgagact catggcactg gcactcaagc aggcgatcct ctggagattg 2160
agagtgtgcg ggaggttttt ggtggtccta aaagacagga ttccatgcac ataggctcaa 2220
tcaaaggcaa cattggtcac tgtgagactg ctgcaggagt cgctggcctt ctcaaagcgc 2280
tcgtcatggt caacaaagct gcaataccgc ctctagcgag tcacaagagc ttgaatccga 2340
agattgccgc cctcgaacct gataagcttg ctatttcaag ttgtcttgaa gactggagag 2400
tctcgccgag agctgcattg gtaaacagct atggcgcggc cggaagtaat tctgctgtcc 2460
tactatgcca ggcccctgac attgacaacg cacctttaca ccgcgtagca accacagagc 2520
atacctatcc aatcatactg agcgctgcat cgaaaccaag tctactttcg aatgctgaaa 2580
acatagcaag ctatttgagg aaagcaactt ccaagtgcac gattgccgat gttgcgttca 2640
ctctcgtcaa acaacgtaaa cgccatccgt tacaatggat aacaatggag tcaagcatcg 2700
acggcttggt caagtccctg gggtctttgc aggacccctc aaatgctccg cagccaaaga 2760
aggtggttat gacattttct ggccaaagtc gacaatcgat tgggctcaac aaagaatggt 2820
atgactcttt ccctctgttc cggcgccatg tgaacgaatg cgacgacttg ctgcagcaga 2880
gcggatttcc ttcctgcaag tctgcaatgt tcgataagga gcctgctcgg gatgttgtgc 2940
cactccagtg tgcgatgttt gctgttcagt acgcatctgc cttgtcttgg atcgattgtg 3000
gacttcaagt agaagctgta attggccaca gcttcggtga gttgacagct ttggcagtgt 3060
cgggtaccct ttccctcaaa gatgctctca atcttgttgc tacccgagct acattgatgc 3120
aatcaaaatg gggcctcac aaagggacca tgctcttgat cagtgcggct actgagatgg 3180
tacgtaaaat cattgcagga aaccgcgatg tcgagatcgc ttgccacaat gcaccaacaa 3240
gccaaattgt tgtaggtacg caagctgcta tctcggaggt tgaaaaagtt ctcgaaaaca 3300
atacggagta tcgcggcatc cagagtcagc gcctcaatgt tacgcacggc ttccattctc 3360
aattcaccga gccattactc gagaatcttt cagagagtgc cagatctcta gtcttccatg 3420
agccgaagat tttgctagag tgttgcactc ttgaagaact gaaccatgtg ggcctgatc 3480 acttagcacg acacactcgg gagcctgttt acttctacca cgctgtacgc cgcctcgagc 3540
agcgtcttgg cacatgtctg tggcttgagg ctggtttcga ctctccgatt ataccaatga 3600
ccaagagggc cgttgaattc ccagagagac acacctttct ggacatgaag actccgagtg 3660
ggacgaatcc cactaagatg ctcactaccg caacgatcaa cctttggcaa aacggtgcta 3720
catcctcctt ctggggcttc catcccatag agacaacaaa cattaaacag gtgtggctgc 3780
caccgtacca attcgatcgg acctcccatt ggatgcctta taccgatcat gctttggaga 3840
tgagcaaaat ccaagccgtc atcagcaatt ctgaaccctt ggtcgaatta tcaactaagc 3900
caccgcgact ggttgagcct cggacgaagc ccagtgagaa aggtgaattc tccatgaaca 3960
cacaagcgcg acgctatacc gaaattgttt ctggtcatgc tgttttgagt cgaccattgt 4020
gtcctgcagc tatgtacatg gaatgcgcaa tcatggccgc acagttgtct attggcaaca 4080
tcgtgggcca ggcgccgtgg ttcgagaatc tgacctttga ggctcccctc ggaatggatc 4140
ctgacaacga caccacagtg gtcttgaagg atgatggttc caaaagcaga tggtcatttg 4200
tcgcgaggag cacgagtagg agcaacccga aacgcaagcc agtcttgcac gccaaagggg 4260
acttcggttt cactacacaa actcaagttc atcgatatga gaggcttgta accgaccgca 4320
tgaggcattt gcagcactct aaaagcgaga cacttaagtc caagcgagct tatggacttt 4380
tctcccgaat cgttcgttat gcagagctat tgaagggaat ttcatcaatt actctaggtg 4440
attcagaagc atctgcaata atcgacgtac cgcttggcgc cagcaccgag gacagctcgg 4500
caacaggact ctgtgattgc gtggcacttg atgccttcat tcaagtggtc ggcttattga 4560
tcaactccgg tgatgattgt gccgaagatg aggtttttgt tgcaactggt gtcgagaact 4620
tctcaatgtc gttggcctgc gacttcgatc gctgcagaac ttggcttgta ttcgccatgt 4680
tcacaccatc gggtaatggt aaagcgatgg gagatgtttt catcctgacg agggacaatg 4740
tcctggtcat gacaatcatg ggtgtacaat ttaccaagct tccgattaca aggctggaga 4800
agctattgga ctcggccaat cccaaagctc acaatacgcc aattttgaag tcaagtcagc 4860
aagactccat cgtatcggcc agcagtagct ctagtacgga gcatagcgat gacgacagcg 4920
aggacgatgg atcacggtct cccagccaca gtgatacctc cgttgacagc gagtcagaag 4980
cgccagcgga caacggtgct gcaaagaaac taaagtctct cattgcatca tatgttggga 5040
tcgctgaaga cgctatttcc gatgatgcaa atattgcgga tcttggagtc gactctcttg 5100
ctgctacaga actagccgac gagatctcga acgacttcgc taaggaaatc gacggcggcg 5160
agcttcccat gatgacattt ggtgaacttt gtcgaatagt ggccccggag atggctgcaa 5220
agcctgcaaa ggcgaaaaag aagattccct acaaaggtaa agatgaagcg actgttgttg 5280
agtcacaccc aggtaaatca cagagtgaga tcaaggactt gaaggctgtg gtggagcctt 5340
tgccaagatc gactcccatg ttatcagata ccaccgtcgt ccgatctgat cctacccaag 5400
tccttcgcca aattgatacc atgtttcagt catctgctga tacattcggc ttcacggact 5460
actggacagc ggtcgcccca aagcagaata agttagtcct ggcatatatt ggcgaggagt 5520
tcagaaagct aggactcgat ctctgggcgg ttcaacctgg agcaaccctt ccacatattg 5580
agtaccttcc aaagcatgaa aaggttgtcc agagactgtg ggatattctt gctgatcatg 5640
gtattgtcta caattatgac gccgcaaagg tgcggtccag caaacctctt ccggacgctc 5700
cttccacggc tctcctcaat gagctcaacg ccttgttccc aaatttcgcc aatgagaatc 5760
ggctaatgtc tgtcacggcg cctcatttcg cggatggttt gaggggaaag actgatcata 5820
ttagtctgct gtttgggagt caacgtggcc aggaatgcct gaatgacttc tataacaatt 5880
cgcctcagtt ggccgtgatg accgatcact tgctcacttt ctttaagcag ctcctgaaag 5940
aagccccact tgaaggttca ctccgaatcc ttgaggtcgg tggcggcttt ggagggacga 6000
caaaacgact agcagaaatg ctggaggcac taggtcagcc ggtcgagtat acgttcacgg 6060
atgtctcgtc catgctagtg aaggaagcaa ggaaaaagtt ttccaaacat tcttggatgg 6120
actttcagtc cttgaatctt gaaaaggacc ctccagcttc tcttcaaagg acatacgata 6180
ttgtgattgg gactaatgta gtgcacgcaa catcgaacat tgtgaattcg acgacacgca 6240
tgcgaagtct tttgaggaag ggtggcttta tcgtcttatc tgaagtcacc cgcattgttg 6300
actggtacga tctggtttat ggactccttg atggctggtg ggccttcaaa gactctagga 6360
cgtatccttt gcagcctgcc gatgactggg tgagagacct catgaaagcg ggattcgaga 6420
ccgcatccta ctcgagggga gactccgagg agtccaacac acagcagctg attattggct 6480
cgaccaggcc aagcaaggta gcgtctacca gcgggctttc ggaagccagg ctaagtaagt 6540
cctatagaat tgagacaatg ccatacaaga tcatcgacga cacggagata ctggcggacg 6600
tcttcttccc agagcatgaa gtggcctcgg aagccatgcc tataggtaat cttctccagt 6660
gtgtctagca atctcacgca gccgctgact tctgacaagc cctcatgatc cacggtggcg 6720
gttttatgac actctccaaa acggccatca gaccctacca gacccaattc ctcgtggaaa 6780
acggctatct tcctatcagc atcgattacc gactttgccc cgagattgat ctaatcgctg 6840
gtccgatgac ggacgttcgt gacgctctaa cctgggtgcg aaaacagctg cctgcgattg 6900
ctcgtacccg cggcatcaat gtggacccaa cgaaagttgt agtcatcgga tggtccacag 6960
gtggtcatct ggccctgact acagcgtgga catgtgagga cattggagaa gagccacctg 7020
ttgcagtcct tagcttctac ggtccaacga acttcgaatc tgaaggtgcg cgtccattga 7080
cactcttttc tgggtgctag tgccacctgt ggtccaaacc gtagcttagg ctgcattcct 7140
acaagatcgc taattgttca taacagacat tgatcggagg cgtgcggaac agtacccaga 7200
acggactatg tcgttcgatc ggatccgcaa gtcattatcc acgaagcctg tgagtatctc 7260
cttgctattg caaattctcc taggccttga cattgcttcc ccatagcatt gttactcttc 7320
tactcactgc taataccctc ttccacacgc agatcacttc ctatgactgt cccaccggca 7380
cagacagcac cggtctcggc tgggtgcgtc ccggcgaccc acgctctgaa ctcgtcttgt 7440
ccctcttcaa agaatctcac ggtctgcaag tgatgcttaa cggtctttct gccgcagatt 7500
tggccaaacc tccgccattg gctaaaattc aggcgatcag cccgatggcg cagctcaagg 7560
ccgggaggta caacgtccca acttttgtaa ttcattcaga ttgtgatgag atcgcgccgt 7620
tcagggatag cgaggctttt gtggaggaac tggcgaggag aggggtgaag actggactag 7680
ggagggtgag gggcaagaag catattcatg acttggcgtt gaagccggag aaggacggat 7740
gggtggacgg tgcgggcgtt ggatatgagt tcattttcga tgttgttgga cgaggcgtta 7800
ggggttga 7808

<210> SEQ ID NO 2
<211> LENGTH: 2500
<212> TYPE: PRT
<213> ORGANISM: Artificial Sequence
<220> FEATURE:
<223> OTHER INFORMATION: Stereocaulon alpinum atr1(QXF68953)

<400> SEQUENCE: 2

```
Met Ala Ser Asn His Glu Glu Leu Pro Ser Met Val Val Phe Ser Pro
1               5                   10                  15

Gln Ser Lys Ala Pro Lys Glu Gly Tyr Leu Asp Glu Leu Arg Ser Tyr
            20                  25                  30

Leu Cys Gly Lys Ala Glu Leu Arg Pro Leu Leu Asp Gly Ile Glu Asn
        35                  40                  45

Leu Pro Asn Thr Trp Ser Ile Phe Ala Gln Arg Asn Ser Asp Ile Ala
    50                  55                  60

Ala Leu Thr Gln Gly Ile Arg Tyr Thr Gln Ala Leu Ser Asp Trp Ala
65                  70                  75                  80

Lys His Gly Thr Ser Ser Gly Ile Ser Asn Val Met Ser Gly Ile Leu
                85                  90                  95

Ser Leu Pro Leu Leu Thr Ile Ile Gln Val Val Gln Tyr Phe Gln Phe
            100                 105                 110

Leu Glu Val Lys Lys Leu Arg His Ser Asp Phe Met Glu Arg Leu Arg
        115                 120                 125

Cys Arg Gly Gly Val Gln Gly Tyr Cys Gly Gly Leu Met Pro Ala Ile
    130                 135                 140

Ala Ile Ala Cys Ser Ala Thr Glu Ala Glu Val Val Thr Asn Ala Val
145                 150                 155                 160

Lys Ala Met Gly Ile Ala Leu Gly Val Gly Ala Tyr Gly Glu Leu Gly
                165                 170                 175

Asp Asp Glu Asn Val Leu Gly Pro Thr Thr Ile Val Val Arg Leu Lys
            180                 185                 190

Gln Glu Gly Gln Gly Gly Asp Ile Ile Lys Asp Phe Pro Asp Ala His
        195                 200                 205

Ile Ser Ala Ile Thr Asp Pro Lys Thr Val Ser Ile Val Gly Ser Ala
    210                 215                 220

Pro Ser Leu Ala Glu Ile Gln Ala Arg Val Lys Ser Asn Gly Met Gln
225                 230                 235                 240

Thr Gln Ala Met His Leu Arg Gly Lys Val His Asn Pro Glu Asn Ala
                245                 250                 255

Asn Leu Ala Leu Glu Leu Cys Met Leu Cys Asp Glu His Glu Glu Leu
            260                 265                 270

Ser Leu Pro Asn Ala Ser His Leu Thr Ala Pro Leu Arg Ser Asn Lys
        275                 280                 285
```

```
Thr Gly Lys Lys Leu Leu Asp Val Ser Leu Thr His Glu Ala Ile Glu
    290                 295                 300

Thr Ile Leu Ala Ser Cys Cys Gln Trp Tyr Asp Leu Leu Lys Gly Val
305                 310                 315                 320

Cys Lys Asp Leu Glu Lys Thr Gly Thr Gln Ser His Leu Phe Ala Ser
                325                 330                 335

Phe Gly Ile Gly Asp Cys Ile Pro Leu Thr Pro Phe His Gln Ala Gly
            340                 345                 350

Leu Gln Ile Thr Lys Leu Asp Val Leu Ser Phe Val Lys Ala Leu Met
        355                 360                 365

Pro Pro Val Leu Pro Met Ser Gly His Asn His Gln Tyr Ala Tyr Pro
    370                 375                 380

Thr Asp Ala Val Ala Val Val Gly Met Ala Cys Arg Leu Pro Gly Ala
385                 390                 395                 400

Asn Ser Val Glu Glu Leu Trp Asp Leu Ile Ser Ser Gly Gly Ser Thr
                405                 410                 415

Val Thr Pro Val Pro Glu Asp Arg Met Asp Ile Ala Gly Ser Phe Arg
            420                 425                 430

Ala Met Gln Asp Pro Lys Trp Ala Ala Lys Gln Gln Trp Trp Gly Asn
        435                 440                 445

Phe Ile Ser Asp Ile Ala Gly Phe Asp His Ser Phe Phe Arg Met Ser
    450                 455                 460

Pro Arg Glu Ala Ala Ser Met Asp Pro Gln Gln Arg Ile Leu Leu Glu
465                 470                 475                 480

Thr Ala Tyr Gln Ala Met Glu Ser Ser Gly Tyr Leu Gly Ser His Arg
                485                 490                 495

Arg Glu Ser Gly Asp Pro Val Gly Val Phe Leu Gly Ala Ser Phe Val
            500                 505                 510

Glu Tyr Leu Asp Asn Thr Ser Ser Asn Pro Pro Thr Ala Tyr Thr Ser
        515                 520                 525

Thr Gly Thr Ile Arg Ala Phe Leu Ser Gly Lys Ile Ser Tyr Tyr Phe
    530                 535                 540

Gly Trp Thr Gly Pro Ser Glu Ile Leu Asp Thr Ala Cys Ser Ser Ser
545                 550                 555                 560

Leu Val Ala Ile Asn Arg Ala Cys Lys Ala Ile Gln Asn Asp Glu Cys
                565                 570                 575

Pro Met Ala Leu Ala Gly Gly Val Asn Leu Ile Thr Gly Ile His Asn
            580                 585                 590

Tyr Leu Asp Leu Ala Lys Ala Gly Phe Leu Ser Pro Ser Gly Gln Cys
        595                 600                 605

Lys Pro Phe Asp Gly Ala Ala Asp Gly Tyr Cys Arg Ser Glu Gly Ala
    610                 615                 620

Gly Leu Val Val Leu Lys Arg Leu Ser Gln Ala Leu Thr Asp Gly Asn
625                 630                 635                 640

Gln Ile Leu Gly Val Ile Thr Gly Ala Ser Thr Asn Gln Gly Gly Leu
                645                 650                 655

Ser Pro Ser Leu Thr Val Pro His Ser Ala Ala Gln Val Lys Leu Tyr
            660                 665                 670

Gln Asn Ile Leu His Gln Ala Gly Met Arg Pro Glu Gln Val Ser Tyr
        675                 680                 685

Cys Glu Thr His Gly Thr Gly Thr Gln Ala Gly Asp Pro Leu Glu Ile
    690                 695                 700
```

```
Glu Ser Val Arg Glu Val Phe Gly Gly Pro Lys Arg Gln Asp Ser Met
705                 710                 715                 720

His Ile Gly Ser Ile Lys Gly Asn Ile Gly His Cys Glu Thr Ala Ala
                725                 730                 735

Gly Val Ala Gly Leu Leu Lys Ala Leu Val Met Val Asn Lys Ala Ala
            740                 745                 750

Ile Pro Pro Leu Ala Ser His Lys Ser Leu Asn Pro Lys Ile Ala Ala
        755                 760                 765

Leu Glu Pro Asp Lys Leu Ala Ile Ser Ser Cys Leu Glu Asp Trp Arg
    770                 775                 780

Val Ser Pro Arg Ala Ala Leu Val Asn Ser Tyr Gly Ala Ala Gly Ser
785                 790                 795                 800

Asn Ser Ala Val Leu Leu Cys Gln Ala Pro Asp Ile Asp Asn Ala Pro
                805                 810                 815

Leu His Arg Val Ala Thr Thr Glu His Thr Tyr Pro Ile Ile Leu Ser
            820                 825                 830

Ala Ala Ser Lys Pro Ser Leu Leu Ser Asn Ala Glu Asn Ile Ala Ser
        835                 840                 845

Tyr Leu Arg Lys Ala Thr Ser Lys Cys Thr Ile Ala Asp Val Ala Phe
    850                 855                 860

Thr Leu Val Lys Gln Arg Lys Arg His Pro Leu Gln Trp Ile Thr Met
865                 870                 875                 880

Glu Ser Ser Ile Asp Gly Leu Val Lys Ser Leu Gly Ser Leu Gln Asp
                885                 890                 895

Pro Ser Asn Ala Pro Gln Pro Lys Lys Val Val Met Thr Phe Ser Gly
            900                 905                 910

Gln Ser Arg Gln Ser Ile Gly Leu Asn Lys Glu Trp Tyr Asp Ser Phe
        915                 920                 925

Pro Leu Phe Arg Arg His Val Asn Glu Cys Asp Asp Leu Leu Gln Gln
    930                 935                 940

Ser Gly Phe Pro Ser Cys Lys Ser Ala Met Phe Asp Lys Glu Pro Ala
945                 950                 955                 960

Arg Asp Val Val Pro Leu Gln Cys Ala Met Phe Ala Val Gln Tyr Ala
                965                 970                 975

Ser Ala Leu Ser Trp Ile Asp Cys Gly Leu Gln Val Glu Ala Val Ile
            980                 985                 990

Gly His Ser Phe Gly Glu Leu Thr Ala Leu Ala Val Ser Gly Thr Leu
        995                 1000                1005

Ser Leu Lys Asp Ala Leu Asn Leu Val Ala Thr Arg Ala Thr Leu Met
    1010                1015                1020

Gln Ser Lys Trp Gly Pro His Lys Gly Thr Met Leu Leu Ile Ser Ala
1025                1030                1035                1040

Ala Thr Glu Met Val Arg Lys Ile Ile Ala Gly Asn Arg Asp Val Glu
                1045                1050                1055

Ile Ala Cys His Asn Ala Pro Thr Ser Gln Ile Val Val Gly Thr Gln
            1060                1065                1070

Ala Ala Ile Ser Glu Val Glu Lys Val Leu Glu Asn Asn Thr Glu Tyr
        1075                1080                1085

Arg Gly Ile Gln Ser Gln Arg Leu Asn Val Thr His Gly Phe His Ser
    1090                1095                1100

Gln Phe Thr Glu Pro Leu Leu Glu Asn Leu Ser Glu Ser Ala Arg Ser
1105                1110                1115                1120
```

-continued

```
Leu Val Phe His Glu Pro Lys Ile Leu Leu Glu Cys Cys Thr Leu Glu
                1125                1130                1135

Glu Leu Asn His Val Gly Pro Asp His Leu Ala Arg His Thr Arg Glu
            1140                1145                1150

Pro Val Tyr Phe Tyr His Ala Val Arg Arg Leu Glu Gln Arg Leu Gly
        1155                1160                1165

Thr Cys Leu Trp Leu Glu Ala Gly Phe Asp Ser Pro Ile Ile Pro Met
    1170                1175                1180

Thr Lys Arg Ala Val Glu Phe Pro Glu Arg His Thr Phe Leu Asp Met
1185                1190                1195                1200

Lys Thr Pro Ser Gly Thr Asn Pro Thr Lys Met Leu Thr Thr Ala Thr
                1205                1210                1215

Ile Asn Leu Trp Gln Asn Gly Ala Thr Ser Ser Phe Trp Gly Phe His
            1220                1225                1230

Pro Ile Glu Thr Thr Asn Ile Lys Gln Val Trp Leu Pro Pro Tyr Gln
        1235                1240                1245

Phe Asp Arg Thr Ser His Trp Met Pro Tyr Thr Asp His Ala Leu Glu
    1250                1255                1260

Met Ser Lys Ile Gln Ala Val Ile Ser Asn Ser Glu Pro Leu Val Glu
1265                1270                1275                1280

Leu Ser Thr Lys Pro Pro Arg Leu Val Glu Pro Arg Thr Lys Pro Ser
                1285                1290                1295

Glu Lys Gly Glu Phe Ser Met Asn Thr Gln Ala Arg Arg Tyr Thr Glu
            1300                1305                1310

Ile Val Ser Gly His Ala Val Leu Ser Arg Pro Leu Cys Pro Ala Ala
        1315                1320                1325

Met Tyr Met Glu Cys Ala Ile Met Ala Ala Gln Leu Ser Ile Gly Asn
    1330                1335                1340

Ile Val Gly Gln Ala Pro Trp Phe Glu Asn Leu Thr Phe Glu Ala Pro
1345                1350                1355                1360

Leu Gly Met Asp Pro Asp Asn Asp Thr Thr Val Val Leu Lys Asp Asp
                1365                1370                1375

Gly Ser Lys Ser Arg Trp Ser Phe Val Ala Arg Ser Thr Ser Arg Ser
            1380                1385                1390

Asn Pro Lys Arg Lys Pro Val Leu His Ala Lys Gly Asp Phe Gly Phe
        1395                1400                1405

Thr Thr Gln Thr Gln Val His Arg Tyr Glu Arg Leu Val Thr Asp Arg
    1410                1415                1420

Met Arg His Leu Gln His Ser Lys Ser Glu Thr Leu Lys Ser Lys Arg
1425                1430                1435                1440

Ala Tyr Gly Leu Phe Ser Arg Ile Val Arg Tyr Ala Glu Leu Leu Lys
                1445                1450                1455

Gly Ile Ser Ser Ile Thr Leu Gly Asp Ser Glu Ala Ser Ala Ile Ile
            1460                1465                1470

Asp Val Pro Leu Gly Ala Ser Thr Glu Asp Ser Ser Ala Thr Gly Leu
        1475                1480                1485

Cys Asp Cys Val Ala Leu Asp Ala Phe Ile Gln Val Val Gly Leu Leu
    1490                1495                1500

Ile Asn Ser Gly Asp Asp Cys Ala Glu Asp Glu Val Phe Val Ala Thr
1505                1510                1515                1520

Gly Val Glu Asn Phe Ser Met Ser Leu Ala Cys Asp Phe Asp Arg Cys
                1525                1530                1535
```

-continued

```
Arg Thr Trp Leu Val Phe Ala Met Phe Thr Pro Ser Gly Asn Gly Lys
            1540                1545                1550

Ala Met Gly Asp Val Phe Ile Leu Thr Arg Asp Asn Val Leu Val Met
        1555                1560                1565

Thr Ile Met Gly Val Gln Phe Thr Lys Leu Pro Ile Thr Arg Leu Glu
    1570                1575                1580

Lys Leu Leu Asp Ser Ala Asn Pro Lys Ala His Asn Thr Pro Ile Leu
1585                1590                1595                1600

Lys Ser Ser Gln Gln Asp Ser Ile Val Ser Ala Ser Ser Ser Ser Ser
                1605                1610                1615

Thr Glu His Ser Asp Asp Asp Ser Glu Asp Asp Gly Ser Arg Ser Pro
            1620                1625                1630

Ser His Ser Asp Thr Ser Val Asp Ser Glu Ser Glu Ala Pro Ala Asp
        1635                1640                1645

Asn Gly Ala Ala Lys Lys Leu Lys Ser Leu Ile Ala Ser Tyr Val Gly
    1650                1655                1660

Ile Ala Glu Asp Ala Ile Ser Asp Asp Ala Asn Ile Ala Asp Leu Gly
1665                1670                1675                1680

Val Asp Ser Leu Ala Ala Thr Glu Leu Ala Asp Glu Ile Ser Asn Asp
                1685                1690                1695

Phe Ala Lys Glu Ile Asp Gly Gly Glu Leu Pro Met Met Thr Phe Gly
            1700                1705                1710

Glu Leu Cys Arg Ile Val Ala Pro Glu Met Ala Ala Lys Pro Ala Lys
        1715                1720                1725

Ala Lys Lys Lys Ile Pro Tyr Lys Gly Lys Asp Glu Ala Thr Val Val
    1730                1735                1740

Glu Ser His Pro Gly Lys Ser Gln Ser Glu Ile Lys Asp Leu Lys Ala
1745                1750                1755                1760

Val Val Glu Pro Leu Pro Arg Ser Thr Pro Met Leu Ser Asp Thr Thr
                1765                1770                1775

Val Val Arg Ser Asp Pro Thr Gln Val Leu Arg Gln Ile Asp Thr Met
            1780                1785                1790

Phe Gln Ser Ser Ala Asp Thr Phe Gly Phe Thr Asp Tyr Trp Thr Ala
        1795                1800                1805

Val Ala Pro Lys Gln Asn Lys Leu Val Leu Ala Tyr Ile Gly Glu Glu
    1810                1815                1820

Phe Arg Lys Leu Gly Leu Asp Leu Trp Ala Val Gln Pro Gly Ala Thr
1825                1830                1835                1840

Leu Pro His Ile Glu Tyr Leu Pro Lys His Glu Lys Val Val Gln Arg
                1845                1850                1855

Leu Trp Asp Ile Leu Ala Asp His Gly Ile Val Tyr Asn Tyr Asp Ala
            1860                1865                1870

Ala Lys Val Arg Ser Ser Lys Pro Leu Pro Asp Ala Pro Ser Thr Ala
        1875                1880                1885

Leu Leu Asn Glu Leu Asn Ala Leu Phe Pro Asn Phe Ala Asn Glu Asn
    1890                1895                1900

Arg Leu Met Ser Val Thr Ala Pro His Phe Ala Asp Gly Leu Arg Gly
1905                1910                1915                1920

Lys Thr Asp His Ile Ser Leu Leu Phe Gly Ser Gln Arg Gly Gln Glu
                1925                1930                1935

Cys Leu Asn Asp Phe Tyr Asn Asn Ser Pro Gln Leu Ala Val Met Thr
            1940                1945                1950
```

```
Asp His Leu Leu Thr Phe Phe Lys Gln Leu Leu Lys Glu Ala Pro Leu
        1955                1960                1965

Glu Gly Ser Leu Arg Ile Leu Glu Val Gly Gly Gly Phe Gly Gly Thr
    1970                1975                1980

Thr Lys Arg Leu Ala Glu Met Leu Glu Ala Leu Gly Gln Pro Val Glu
1985                1990                1995                2000

Tyr Thr Phe Thr Asp Val Ser Ser Met Leu Val Lys Glu Ala Arg Lys
                2005                2010                2015

Lys Phe Ser Lys His Ser Trp Met Asp Phe Gln Ser Leu Asn Leu Glu
            2020                2025                2030

Lys Asp Pro Pro Ala Ser Leu Gln Arg Thr Tyr Asp Ile Val Ile Gly
        2035                2040                2045

Thr Asn Val Val His Ala Thr Ser Asn Ile Val Asn Ser Thr Thr Arg
    2050                2055                2060

Met Arg Ser Leu Leu Arg Lys Gly Gly Phe Ile Val Leu Ser Glu Val
2065                2070                2075                2080

Thr Arg Ile Val Asp Trp Tyr Asp Leu Val Tyr Gly Leu Leu Asp Gly
                2085                2090                2095

Trp Trp Ala Phe Lys Asp Ser Arg Thr Tyr Pro Leu Gln Pro Ala Asp
            2100                2105                2110

Asp Trp Val Arg Asp Leu Met Lys Ala Gly Phe Glu Thr Ala Ser Tyr
        2115                2120                2125

Ser Arg Gly Asp Ser Glu Glu Ser Asn Thr Gln Gln Leu Ile Ile Gly
    2130                2135                2140

Ser Thr Arg Pro Ser Lys Val Ala Ser Thr Ser Gly Leu Ser Glu Ala
2145                2150                2155                2160

Arg Leu Ser Lys Ser Tyr Arg Ile Glu Thr Met Pro Tyr Lys Ile Ile
                2165                2170                2175

Asp Asp Thr Glu Ile Leu Ala Asp Val Phe Phe Pro Glu His Glu Val
            2180                2185                2190

Ala Ser Glu Ala Met Pro Ile Ala Leu Met Ile His Gly Gly Gly Phe
        2195                2200                2205

Met Thr Leu Ser Lys Thr Ala Ile Arg Pro Tyr Gln Thr Gln Phe Leu
    2210                2215                2220

Val Glu Asn Gly Tyr Leu Pro Ile Ser Ile Asp Tyr Arg Leu Cys Pro
2225                2230                2235                2240

Glu Ile Asp Leu Ile Ala Gly Pro Met Thr Asp Val Arg Asp Ala Leu
                2245                2250                2255

Thr Trp Val Arg Lys Gln Leu Pro Ala Ile Ala Arg Thr Arg Gly Ile
            2260                2265                2270

Asn Val Asp Pro Thr Lys Val Val Val Ile Gly Trp Ser Thr Gly Gly
        2275                2280                2285

His Leu Ala Leu Thr Thr Ala Trp Thr Cys Glu Asp Ile Gly Glu Glu
    2290                2295                2300

Pro Pro Val Ala Val Leu Ser Phe Tyr Gly Pro Thr Asn Phe Glu Ser
2305                2310                2315                2320

Glu Asp Ile Asp Arg Arg Arg Ala Glu Gln Tyr Pro Glu Arg Thr Met
                2325                2330                2335

Ser Phe Asp Arg Ile Arg Lys Ser Leu Ser Thr Lys Pro Ile Thr Ser
            2340                2345                2350

Tyr Asp Cys Pro Thr Gly Thr Asp Ser Thr Gly Leu Gly Trp Val Arg
        2355                2360                2365
```

```
Pro Gly Asp Pro Arg Ser Glu Leu Val Leu Ser Leu Phe Lys Glu Ser
    2370                2375                2380

His Gly Leu Gln Val Met Leu Asn Gly Leu Ser Ala Ala Asp Leu Ala
2385                2390                2395                2400

Lys Pro Pro Pro Leu Ala Lys Ile Gln Ala Ile Ser Pro Met Ala Gln
                2405                2410                2415

Leu Lys Ala Gly Arg Tyr Asn Val Pro Thr Phe Val Ile His Ser Asp
            2420                2425                2430

Cys Asp Glu Ile Ala Pro Phe Arg Asp Ser Glu Ala Phe Val Glu Glu
        2435                2440                2445

Leu Ala Arg Arg Gly Val Lys Thr Gly Leu Gly Arg Val Arg Gly Lys
    2450                2455                2460

Lys His Ile His Asp Leu Ala Leu Lys Pro Glu Lys Asp Gly Trp Val
2465                2470                2475                2480

Asp Gly Ala Gly Val Gly Tyr Glu Phe Ile Phe Asp Val Val Gly Arg
                2485                2490                2495

Gly Val Arg Gly
            2500


<210> SEQ ID NO 3
<211> LENGTH: 1761
<212> TYPE: DNA
<213> ORGANISM: Artificial Sequence
<220> FEATURE:
<223> OTHER INFORMATION: Stereocaulon alpinum atr2 gene(MZ277878)

<400> SEQUENCE: 3

atggctctcc tagacacaat tgaactgttc tccaacttct cccttagtgg agtgttcgct      60

ggcctagttc tagcttctct cctcgtaagt tcaaccactg ttacgtcgtc aaaatgtgcc     120

agccttccct ttgcgagaac tgacacataa gcaactagac cacaacttac tgcatttgga     180

acatcttcta caatatttac cttcatccct tgaaaggtta ccctggccca aaattcctca     240

caacttctcg gcttccatat ctcaaatgga tgttctcagg aacccttgtg cccaatttcc     300

aaaggctcca tgagcagtac ggtcctgttg ttcgtgttgc gcccaacgag ctctcgtaca     360

tcaacccgga agccttgaaa accatctacg gccaccgtca accaggcgag ggtttcgca      420

agaatccagc attcttccag ccagctacga atggcgttca ttccatcttg acctccgaag     480

gtgacgctca tagtagtgtc cgccggaaga tcctgcccgc tttctcggat aaggcgcttg     540

cggaacagca ggacatcctc cagcatttca cagatctgtt gatccggaaa ttgcgcgaga     600

gagtcgaagc atccaaaagc tcagaacctg ttgacatgtt cgaatggtac atctggacta     660

ccttcgactt gattggagat ctcgcatttg gcgagccgtt caactgcctc gaagcagcta     720

gctttacaga atgggtcgcc cttgtgttca acgcgtttaa gactttttgcg ttcatcaaca    780

tcaggtaagc aaggtagact caccccgcaa cgaataaaag aaacgcgctt acgaaaccga     840

actagcaaac agctagctcc ccttgacaag ctagtcagac tgatgatccc aaagtccatg     900

aaagcccggc aagacaaagt cttctccctg aacgtcgcca aagtcgaccg ccgcattgct     960

tccaaagcag accgtccaga cttcctatcg tacattatta agggcaagga cggggtagca    1020

atggcacttc cagaactcta cgcaaattcc acgctccttg tcctcgccgg tagcgagagc    1080

acagcatctg gcttggctgg cattaccttt gagctactca agcaccgaga ggctcagaag    1140

aaggccgtgg aagagatacg cagcgctttc aaaaccgaag atgagattgt acctgagagc    1200

gtcaagcgac ttccatacct tgcggccatg gtttccgaag ggctccgaat gtatccgccc    1260
```

```
ttcccagagg gacttcctcg tcttacacca cggcaagggg ctcagatctg tggccaatgg   1320

gtccctggag gagtaagcta tgacccccat cctccgggac tagctaatct tctcatatag   1380

acatatgtgc aatttagcac ccacgccgct caccgcgcca gcgccaattt tacagacccg   1440

aatgtcttcg cccctgagcg ctggcttggc gacacgaaat tcgcgtcgga tatcaaagaa   1500

gcttcgcagc ccttctcgat aggtccacgt agctgcattg gcaggaagtg agtactttgt   1560

tcgcctcatt tgcacgaaga gtactaatta tacgggaaac ccagtcttgc gtaccttgaa   1620

atgcgcttga ttctagcgcg tatgttgtgg agcttcgaca tgcaactcac tcccgaatgc   1680

gaagactggg acgaccagaa tagctggatc cagtgggaca agaaaccttt gatggtgaag   1740

ttgtcgcttg tcaaaagata g                                               1761


<210> SEQ ID NO 4
<211> LENGTH: 506
<212> TYPE: PRT
<213> ORGANISM: Artificial Sequence
<220> FEATURE:
<223> OTHER INFORMATION: Stereocaulon alpinum atr2(QXF68952)

<400> SEQUENCE: 4

Met Ala Leu Leu Asp Thr Ile Glu Leu Phe Ser Asn Phe Ser Leu Ser
1               5                   10                  15

Gly Val Phe Ala Gly Leu Val Leu Ala Ser Leu Leu Thr Thr Thr Tyr
            20                  25                  30

Cys Ile Trp Asn Ile Phe Tyr Asn Ile Tyr Leu His Pro Leu Lys Gly
        35                  40                  45

Tyr Pro Gly Pro Lys Phe Leu Thr Thr Ser Arg Leu Pro Tyr Leu Lys
    50                  55                  60

Trp Met Phe Ser Gly Thr Leu Val Pro Asn Phe Gln Arg Leu His Glu
65                  70                  75                  80

Gln Tyr Gly Pro Val Val Arg Val Ala Pro Asn Glu Leu Ser Tyr Ile
                85                  90                  95

Asn Pro Glu Ala Leu Lys Thr Ile Tyr Gly His Arg Gln Pro Gly Glu
            100                 105                 110

Gly Phe Arg Lys Asn Pro Ala Phe Phe Gln Pro Ala Thr Asn Gly Val
        115                 120                 125

His Ser Ile Leu Thr Ser Glu Gly Asp Ala His Ser Ser Val Arg Arg
    130                 135                 140

Lys Ile Leu Pro Ala Phe Ser Asp Lys Ala Leu Ala Glu Gln Gln Asp
145                 150                 155                 160

Ile Leu Gln His Phe Thr Asp Leu Leu Ile Arg Lys Leu Arg Glu Arg
                165                 170                 175

Val Glu Ala Ser Lys Ser Ser Glu Pro Val Asp Met Phe Glu Trp Tyr
            180                 185                 190

Ile Trp Thr Thr Phe Asp Leu Ile Gly Asp Leu Ala Phe Gly Glu Pro
        195                 200                 205

Phe Asn Cys Leu Glu Ala Ala Ser Phe Thr Glu Trp Val Ala Leu Val
    210                 215                 220

Phe Asn Ala Phe Lys Thr Phe Ala Phe Ile Asn Ile Ser Lys Gln Leu
225                 230                 235                 240

Ala Pro Leu Asp Lys Leu Val Arg Leu Met Ile Pro Lys Ser Met Lys
                245                 250                 255

Ala Arg Gln Asp Lys Val Phe Ser Leu Asn Val Ala Lys Val Asp Arg
            260                 265                 270
```

-continued

```
Arg Ile Ala Ser Lys Ala Asp Arg Pro Asp Phe Leu Ser Tyr Ile Ile
        275                 280                 285

Lys Gly Lys Asp Gly Val Ala Met Ala Leu Pro Glu Leu Tyr Ala Asn
    290                 295                 300

Ser Thr Leu Leu Val Leu Ala Gly Ser Glu Ser Thr Ala Ser Gly Leu
305                 310                 315                 320

Ala Gly Ile Thr Phe Glu Leu Leu Lys His Arg Glu Ala Gln Lys Lys
                325                 330                 335

Ala Val Glu Glu Ile Arg Ser Ala Phe Lys Thr Glu Asp Glu Ile Val
            340                 345                 350

Pro Glu Ser Val Lys Arg Leu Pro Tyr Leu Ala Ala Met Val Ser Glu
        355                 360                 365

Gly Leu Arg Met Tyr Pro Pro Phe Pro Glu Gly Leu Pro Arg Leu Thr
    370                 375                 380

Pro Arg Gln Gly Ala Gln Ile Cys Gly Gln Trp Val Pro Gly Gly Thr
385                 390                 395                 400

Tyr Val Gln Phe Ser Thr His Ala Ala His Arg Ala Ser Ala Asn Phe
                405                 410                 415

Thr Asp Pro Asn Val Phe Ala Pro Glu Arg Trp Leu Gly Asp Thr Lys
            420                 425                 430

Phe Ala Ser Asp Ile Lys Glu Ala Ser Gln Pro Phe Ser Ile Gly Pro
        435                 440                 445

Arg Ser Cys Ile Gly Arg Asn Leu Ala Tyr Leu Glu Met Arg Leu Ile
    450                 455                 460

Leu Ala Arg Met Leu Trp Ser Phe Asp Met Gln Leu Thr Pro Glu Cys
465                 470                 475                 480

Glu Asp Trp Asp Asp Gln Asn Ser Trp Ile Gln Trp Asp Lys Lys Pro
                485                 490                 495

Leu Met Val Lys Leu Ser Leu Val Lys Arg
            500                 505
```

<210> SEQ ID NO 5
<211> LENGTH: 1254
<212> TYPE: DNA
<213> ORGANISM: Artificial Sequence
<220> FEATURE:
<223> OTHER INFORMATION: Stereocaulon alpinum atr3 gene(MZ277877)

<400> SEQUENCE: 5

```
atgacttccg ttgatacaat gcctccaccg atggttcgcc tcgagagtca gcctgacgac      60

ttgatgggct cttctgatgt cgcggacgtt tcagaccttc ttccaggcca tacaaatgga     120

ctcgaggatg aagtgaaaat tccagcaacc aatggactca agagccatcc agtggttacg     180

acaggaacag aaaaaaccgg tgtgatgccg ccccttcagc ccgaaagcaa gaagaacaac     240

aaaggcgttc cgtggtaaga cctggacata caccgctctt tttgtcaagc catgactgtt     300

acgacttcct gttgttttct atcatttctc tgccagtagt gctgaggtag acaggtatca     360

cgcctcaccg aacgatatcg atcccgtgac tcgcggtctg ctcgaaaatt acagcaaaat     420

cccctcggat caagtacagc agcacgttat cgcaattgta agtttccaaa ggttactcct     480

tgatgttctg caaccggatt gcagttggcg cactagatgg ctctctccct agacaagcat     540

cgctaaaacc gtctttttct cccaaaacag cgcgaaaaag cctgggacgt ctacccctac     600

ccctgcatcg gccaattcct cttcctgaac ctaaccataa acctctcccc ctactacccg     660

tccctcgtct cccgcctccg cgatcaaaat caaacactcc tcgacctcgg ctgctgcttc     720
```

-continued gcccaagacg tccgcaaact cgtctctgat ggcgccccga gtcaaaacat ctacggcgcc 780
gacctctatg gcgagttcat ggatctaggc tttgaactct ttcgcgaccg aaagacgctc 840
aaaagcacgt ttttcccgac tgatatacta aacgagcggg atctgctgtt gaagggcttg 900
gatggcgaga tggatgttgt ttatttgggg ctgtttttgc atcattttga ttttgagact 960
tgtgtcaaag tttgtacgcg cgttactagg ctcctgaagc ccaagccggg gagtctggtt 1020
atgggggtcc aggtggggag tttggtgggt gatactaaac ccattcctat tcctagtggt 1080
gggattttgt ggaggcatga tattgcgagt cttgaaaggg tttgggagga ggttggagcg 1140
ctgacgggga cgaagtggaa ggttgaggct aggttggaga ggggcaaagg gttcggggag 1200
aagtggcagc ttgaggggac gaggaggttg gggtttgagg tttataggct ttga 1254

<210> SEQ ID NO 6
<211> LENGTH: 346
<212> TYPE: PRT
<213> ORGANISM: Artificial Sequence
<220> FEATURE:
<223> OTHER INFORMATION: Stereocaulon alpinum atr3(QXF68951)

<400> SEQUENCE: 6

Met Thr Ser Val Asp Thr Met Pro Pro Pro Met Val Arg Leu Glu Ser
1               5                   10                  15

Gln Pro Asp Asp Leu Met Gly Ser Ser Asp Val Ala Asp Val Ser Asp
            20                  25                  30

Leu Leu Pro Gly His Thr Asn Gly Leu Glu Asp Glu Val Lys Ile Pro
        35                  40                  45

Ala Thr Asn Gly Leu Lys Ser His Pro Val Val Thr Thr Gly Thr Glu
    50                  55                  60

Lys Thr Gly Val Met Pro Pro Leu Gln Pro Glu Ser Lys Lys Asn Asn
65                  70                  75                  80

Lys Gly Val Pro Trp Tyr His Ala Ser Pro Asn Asp Ile Asp Pro Val
                85                  90                  95

Thr Arg Gly Leu Leu Glu Asn Tyr Ser Lys Ile Pro Ser Asp Gln Val
            100                 105                 110

Gln Gln His Val Ile Ala Ile Arg Glu Lys Ala Trp Asp Val Tyr Pro
        115                 120                 125

Tyr Pro Cys Ile Gly Gln Phe Leu Phe Leu Asn Leu Thr Ile Asn Leu
    130                 135                 140

Ser Pro Tyr Tyr Pro Ser Leu Val Ser Arg Leu Arg Asp Gln Asn Gln
145                 150                 155                 160

Thr Leu Leu Asp Leu Gly Cys Cys Phe Ala Gln Asp Val Arg Lys Leu
                165                 170                 175

Val Ser Asp Gly Ala Pro Ser Gln Asn Ile Tyr Gly Ala Asp Leu Tyr
            180                 185                 190

Gly Glu Phe Met Asp Leu Gly Phe Glu Leu Phe Arg Asp Arg Lys Thr
        195                 200                 205

Leu Lys Ser Thr Phe Phe Pro Thr Asp Ile Leu Asn Glu Arg Asp Leu
    210                 215                 220

Leu Leu Lys Gly Leu Asp Gly Glu Met Asp Val Val Tyr Leu Gly Leu
225                 230                 235                 240

Phe Leu His His Phe Asp Phe Glu Thr Cys Val Lys Val Cys Thr Arg
                245                 250                 255

Val Thr Arg Leu Leu Lys Pro Lys Pro Gly Ser Leu Val Met Gly Val
            260                 265                 270

```
Gln Val Gly Ser Leu Val Gly Asp Thr Lys Pro Ile Pro Ile Pro Ser
        275                 280                 285

Gly Gly Ile Leu Trp Arg His Asp Ile Ala Ser Leu Glu Arg Val Trp
    290                 295                 300

Glu Glu Val Gly Ala Leu Thr Gly Thr Lys Trp Lys Val Glu Ala Arg
305                 310                 315                 320

Leu Glu Arg Gly Lys Gly Phe Gly Glu Lys Trp Gln Leu Glu Gly Thr
                325                 330                 335

Arg Arg Leu Gly Phe Glu Val Tyr Arg Leu
            340                 345


<210> SEQ ID NO 7
<211> LENGTH: 27
<212> TYPE: DNA
<213> ORGANISM: Artificial Sequence
<220> FEATURE:
<223> OTHER INFORMATION: Sol1PpDS33_fwd

<400> SEQUENCE: 7

agatctcggc acgttttgat cgcaaag                                          27


<210> SEQ ID NO 8
<211> LENGTH: 32
<212> TYPE: DNA
<213> ORGANISM: Artificial Sequence
<220> FEATURE:
<223> OTHER INFORMATION: Sol1PpDS33_rev

<400> SEQUENCE: 8

aagcttagta atatctggcg atgaagcgtc ag                                    32


<210> SEQ ID NO 9
<211> LENGTH: 38
<212> TYPE: DNA
<213> ORGANISM: Artificial Sequence
<220> FEATURE:
<223> OTHER INFORMATION: Inf_Sta046440_fwd

<400> SEQUENCE: 9

cagatattac taagctcatg gcgtctaacc atgaggag                              38


<210> SEQ ID NO 10
<211> LENGTH: 44
<212> TYPE: DNA
<213> ORGANISM: Artificial Sequence
<220> FEATURE:
<223> OTHER INFORMATION: Inf_Sta046440_rev

<400> SEQUENCE: 10

gtaacgttaa gtggatcctt acaactaaag ctctcaatca accc                       44


<210> SEQ ID NO 11
<211> LENGTH: 20
<212> TYPE: DNA
<213> ORGANISM: Artificial Sequence
<220> FEATURE:
<223> OTHER INFORMATION: Sta046440_check1F

<400> SEQUENCE: 11

ggacgatgag aacgtcctag                                                  20


<210> SEQ ID NO 12
<211> LENGTH: 19
<212> TYPE: DNA
```

<213> ORGANISM: Artificial Sequence
<220> FEATURE:
<223> OTHER INFORMATION: Sta046440_check2F

<400> SEQUENCE: 12
cgagtcaggt gatccagtg 19

<210> SEQ ID NO 13
<211> LENGTH: 19
<212> TYPE: DNA
<213> ORGANISM: Artificial Sequence
<220> FEATURE:
<223> OTHER INFORMATION: Sta046440_check3F

<400> SEQUENCE: 13
ccaatcatac tgagcgctg 19

<210> SEQ ID NO 14
<211> LENGTH: 19
<212> TYPE: DNA
<213> ORGANISM: Artificial Sequence
<220> FEATURE:
<223> OTHER INFORMATION: Sta046440_check4F

<400> SEQUENCE: 14
cacatgtctg tggcttgag 19

<210> SEQ ID NO 15
<211> LENGTH: 18
<212> TYPE: DNA
<213> ORGANISM: Artificial Sequence
<220> FEATURE:
<223> OTHER INFORMATION: Sta046440_check5F

<400> SEQUENCE: 15
caactccggt gatgattg 18

<210> SEQ ID NO 16
<211> LENGTH: 20
<212> TYPE: DNA
<213> ORGANISM: Artificial Sequence
<220> FEATURE:
<223> OTHER INFORMATION: Sta046440_check6F

<400> SEQUENCE: 16
caacccttcc acatattgag 20

<210> SEQ ID NO 17
<211> LENGTH: 23
<212> TYPE: DNA
<213> ORGANISM: Artificial Sequence
<220> FEATURE:
<223> OTHER INFORMATION: pII99_sol5_fwd

<400> SEQUENCE: 17
gaattcagag cgacagtgaa agc 23

<210> SEQ ID NO 18
<211> LENGTH: 37
<212> TYPE: DNA
<213> ORGANISM: Artificial Sequence
<220> FEATURE:
<223> OTHER INFORMATION: pII99_sol5_rev

<400> SEQUENCE: 18
agatctagct agcttggcgt gatgtcagtc aatgctg 37

<210> SEQ ID NO 19
<211> LENGTH: 27
<212> TYPE: DNA
<213> ORGANISM: Artificial Sequence
<220> FEATURE:
<223> OTHER INFORMATION: pII99_tef1a_fwd

<400> SEQUENCE: 19
gaattccagc cgagacagca gaatcac 27

<210> SEQ ID NO 20
<211> LENGTH: 41
<212> TYPE: DNA
<213> ORGANISM: Artificial Sequence
<220> FEATURE:
<223> OTHER INFORMATION: pII99_tef1a_rev

<400> SEQUENCE: 20
agatctagct agcgtgttat gttttgtgga atataaaagg g 41

<210> SEQ ID NO 21
<211> LENGTH: 40
<212> TYPE: DNA
<213> ORGANISM: Artificial Sequence
<220> FEATURE:
<223> OTHER INFORMATION: Inf95_Sta04642_fwd

<400> SEQUENCE: 21
atcacgccaa gctagcacga tgacttccgt tgatacaatg 40

<210> SEQ ID NO 22
<211> LENGTH: 41
<212> TYPE: DNA
<213> ORGANISM: Artificial Sequence
<220> FEATURE:
<223> OTHER INFORMATION: Inf98_Sta04642_fwd

<400> SEQUENCE: 22
aaacataaca cgctagcacg atgacttccg ttgatacaat g 41

<210> SEQ ID NO 23
<211> LENGTH: 39
<212> TYPE: DNA
<213> ORGANISM: Artificial Sequence
<220> FEATURE:
<223> OTHER INFORMATION: Inf99_Sta04642_rev

<400> SEQUENCE: 23
ggagaccggc agatcccgtc acatgtccgt cataataac 39

<210> SEQ ID NO 24
<211> LENGTH: 42
<212> TYPE: DNA
<213> ORGANISM: Artificial Sequence
<220> FEATURE:
<223> OTHER INFORMATION: Inf98_Sta04643_fwd

<400> SEQUENCE: 24
aaacataaca cgctagaacc atggctctcc tagacacaat tg 42

<210> SEQ ID NO 25
<211> LENGTH: 41
<212> TYPE: DNA
<213> ORGANISM: Artificial Sequence
<220> FEATURE:

<223> OTHER INFORMATION: Inf95_Sta04643_fwd

<400> SEQUENCE: 25
atcacgccaa gctagaacca tggctctcct agacacaatt g 41

<210> SEQ ID NO 26
<211> LENGTH: 39
<212> TYPE: DNA
<213> ORGANISM: Artificial Sequence
<220> FEATURE:
<223> OTHER INFORMATION: Inf99_Sta04643_rev

<400> SEQUENCE: 26
ggagaccggc agatcgagga gcaaaggaac aaggaacag 39

<210> SEQ ID NO 27
<211> LENGTH: 22
<212> TYPE: DNA
<213> ORGANISM: Artificial Sequence
<220> FEATURE:
<223> OTHER INFORMATION: pII99_MK5

<400> SEQUENCE: 27
cgtcaagaga cctacgagac tg 22

<210> SEQ ID NO 28
<211> LENGTH: 25
<212> TYPE: DNA
<213> ORGANISM: Artificial Sequence
<220> FEATURE:
<223> OTHER INFORMATION: pII99_MK3

<400> SEQUENCE: 28
gctatacttc taggtcttgg aagag 25

<210> SEQ ID NO 29
<211> LENGTH: 38
<212> TYPE: DNA
<213> ORGANISM: Artificial Sequence
<220> FEATURE:
<223> OTHER INFORMATION: Inf_BLE_pII99_fwd

<400> SEQUENCE: 29
gtaggtctct tgacgcatta agacctcagc gctagtgg 38

<210> SEQ ID NO 30
<211> LENGTH: 39
<212> TYPE: DNA
<213> ORGANISM: Artificial Sequence
<220> FEATURE:
<223> OTHER INFORMATION: Inf_BLE_pII99_rev

<400> SEQUENCE: 30
gacctagaag tatagcggtg ttacggagca ttcactagg 39

<210> SEQ ID NO 31
<211> LENGTH: 23
<212> TYPE: DNA
<213> ORGANISM: Artificial Sequence
<220> FEATURE:
<223> OTHER INFORMATION: L5

<400> SEQUENCE: 31
gaggtcttca caccacaagt tcg 23

<210> SEQ ID NO 32
<211> LENGTH: 52
<212> TYPE: DNA
<213> ORGANISM: Artificial Sequence
<220> FEATURE:
<223> OTHER INFORMATION: L3

<400> SEQUENCE: 32
ggcaaaggaa tagagtagat gccgaccggg ctcttgcgta gtggtacaga tg 52

<210> SEQ ID NO 33
<211> LENGTH: 51
<212> TYPE: DNA
<213> ORGANISM: Artificial Sequence
<220> FEATURE:
<223> OTHER INFORMATION: R5

<400> SEQUENCE: 33
gttgacctcc actagctcca gccaagcgaa taggtaacaa agccagccga g 51

<210> SEQ ID NO 34
<211> LENGTH: 23
<212> TYPE: DNA
<213> ORGANISM: Artificial Sequence
<220> FEATURE:
<223> OTHER INFORMATION: R3

<400> SEQUENCE: 34
gagaattgcg gcgcaggatg ttc 23

<210> SEQ ID NO 35
<211> LENGTH: 24
<212> TYPE: DNA
<213> ORGANISM: Artificial Sequence
<220> FEATURE:
<223> OTHER INFORMATION: N5

<400> SEQUENCE: 35
ctgactttct tcttgcagcc ctgc 24

<210> SEQ ID NO 36
<211> LENGTH: 24
<212> TYPE: DNA
<213> ORGANISM: Artificial Sequence
<220> FEATURE:
<223> OTHER INFORMATION: N3

<400> SEQUENCE: 36
ctaacgatgt cgttagtcgc cttg 24

<210> SEQ ID NO 37
<211> LENGTH: 21
<212> TYPE: DNA
<213> ORGANISM: Artificial Sequence
<220> FEATURE:
<223> OTHER INFORMATION: HYG-F

<400> SEQUENCE: 37
gcttggctgg agctagtgga g 21

<210> SEQ ID NO 38
<211> LENGTH: 24
<212> TYPE: DNA
<213> ORGANISM: Artificial Sequence
<220> FEATURE:
<223> OTHER INFORMATION: HYG-R

<400> SEQUENCE: 38
cggtcggcat ctactctatt cctt 24

<210> SEQ ID NO 39
<211> LENGTH: 25
<212> TYPE: DNA
<213> ORGANISM: Artificial Sequence
<220> FEATURE:
<223> OTHER INFORMATION: YG-F

<400> SEQUENCE: 39
cgatgtagga gggcgtggat atgtc 25

<210> SEQ ID NO 40
<211> LENGTH: 26
<212> TYPE: DNA
<213> ORGANISM: Artificial Sequence
<220> FEATURE:
<223> OTHER INFORMATION: HY-R

<400> SEQUENCE: 40
tgtagtgtat tgaccgattc cttgcg 26

<210> SEQ ID NO 41
<211> LENGTH: 20
<212> TYPE: DNA
<213> ORGANISM: Artificial Sequence
<220> FEATURE:
<223> OTHER INFORMATION: P1_fwd

<400> SEQUENCE: 41
ggacgatgag aacgtcctag 20

<210> SEQ ID NO 42
<211> LENGTH: 20
<212> TYPE: DNA
<213> ORGANISM: Artificial Sequence
<220> FEATURE:
<223> OTHER INFORMATION: P1_rev

<400> SEQUENCE: 42
gagagttcct catgctcgtc 20

<210> SEQ ID NO 43
<211> LENGTH: 22
<212> TYPE: DNA
<213> ORGANISM: Artificial Sequence
<220> FEATURE:
<223> OTHER INFORMATION: P2_fwd

<400> SEQUENCE: 43
catcgacgac acggagatac tg 22

<210> SEQ ID NO 44
<211> LENGTH: 23
<212> TYPE: DNA
<213> ORGANISM: Artificial Sequence
<220> FEATURE:
<223> OTHER INFORMATION: P2_rev

<400> SEQUENCE: 44
gaccgtgaga ttctttgaag agg 23

<210> SEQ ID NO 45
<211> LENGTH: 22

```
<212> TYPE: DNA
<213> ORGANISM: Artificial Sequence
<220> FEATURE:
<223> OTHER INFORMATION: Actin1_fwd

<400> SEQUENCE: 45

caatggttcg ggtatgtgca ag                                            22


<210> SEQ ID NO 46
<211> LENGTH: 22
<212> TYPE: DNA
<213> ORGANISM: Artificial Sequence
<220> FEATURE:
<223> OTHER INFORMATION: Actin1_rev

<400> SEQUENCE: 46

gaagagcgaa accctcgtag at                                            22
```